(12) United States Patent
Caldwell

(10) Patent No.: US 12,429,985 B2
(45) Date of Patent: *Sep. 30, 2025

(54) SIMULTANEOUS TIME DOMAIN DIFFERENTIAL SENSING AND ELECTRIC FIELD SENSING

(71) Applicant: ALSENTIS, LLC, Holland, MI (US)

(72) Inventor: David W. Caldwell, Holland, MI (US)

(73) Assignee: ALSENTIS, LLC, Holland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/351,430

(22) Filed: Jul. 12, 2023

(65) Prior Publication Data

US 2023/0355911 A1 Nov. 9, 2023

Related U.S. Application Data

(63) Continuation of application No. 17/401,144, filed on Aug. 12, 2021, now Pat. No. 11,730,910, which is a
(Continued)

(51) Int. Cl.
*G06F 3/044* (2006.01)
*A61M 16/00* (2006.01)
(Continued)

(52) U.S. Cl.
CPC ......... *G06F 3/044* (2013.01); *A61M 16/0057* (2013.01); *A61M 16/06* (2013.01);
(Continued)

(58) Field of Classification Search
CPC .... G06F 3/044; G06F 3/04166; G06F 3/0443; G06F 3/04182; A61M 16/0057; A61M 16/06; A61M 16/0816; A61M 16/208; A61M 2205/42; A61M 2206/11; H03K 17/9622; H03K 2017/9606;
(Continued)

(56) References Cited

U.S. PATENT DOCUMENTS 4,766,368 A 8/1988 Cox
5,594,222 A 1/1997 Caldwell
(Continued)

FOREIGN PATENT DOCUMENTS

EP 1936807 A1 6/2008
WO 9613098 A1 5/1996
(Continued)

*Primary Examiner* — Sahlu Okebato
(74) *Attorney, Agent, or Firm* — Ingrassia Fisher & Lorenz, LLP

(57) ABSTRACT

Systems and methods for determining a touch input are provided. The systems and methods generally include measuring the peak voltage at an electrode over a measurement period and determining a touch input based on the peak voltage. The systems and methods can conserve computing resources by deferring digital signal processing until after a peak electrode capacitance has been sampled. The systems and methods are suitable for capacitive sensors using self-capacitance and capacitive sensors using mutual capacitance. The systems and methods are also suitable for capacitive buttons, track pads, and touch screens, among other implementations.

18 Claims, 49 Drawing Sheets

Related U.S. Application Data continuation of application No. 15/122,541, filed as application No. PCT/US2015/018593 on Mar. 4, 2015, now Pat. No. 11,561,652.

(60) Provisional application No. 61/947,641, filed on Mar. 4, 2014.

(51) Int. Cl.

| | | |
|---|---|---|
| *A61M 16/06* | (2006.01) | |
| *A61M 16/08* | (2006.01) | |
| *A61M 16/20* | (2006.01) | |
| *G06F 3/041* | (2006.01) | |
| *H03K 17/96* | (2006.01) | |

(52) U.S. Cl.
CPC ...... *A61M 16/0816* (2013.01); *A61M 16/208* (2013.01); *G06F 3/04166* (2019.05); *H03K 17/9622* (2013.01); *A61M 2205/42* (2013.01); *A61M 2206/11* (2013.01); *H03K 2017/9606* (2013.01); *H03K 2017/9613* (2013.01); *H03K 2217/94094* (2013.01); *H03K 2217/960725* (2013.01); *H03K 2217/96073* (2013.01); *H03K 2217/96074* (2013.01); *H03K 2217/960775* (2013.01)

(58) Field of Classification Search
CPC . H03K 2017/9613; H03K 2217/94094; H03K 2217/960725; H03K 2217/96073; H03K 2217/96074; H03K 2217/960775
See application file for complete search history.

(56) References Cited

U.S. PATENT DOCUMENTS

| | | |
|---|---|---|
| 2002/0130848 A1 | 9/2002 | Sims |
| 2005/0073351 A1 | 4/2005 | Ko et al. |
| 2006/0186894 A1 | 8/2006 | Iwabuchi et al. |
| 2008/0251299 A1 | 10/2008 | Liao |
| 2011/0084936 A1* | 4/2011 | Chang .................. G06F 3/0446 |
| | | 345/174 |
| 2011/0115717 A1 | 5/2011 | Hable et al. |
| 2012/0068760 A1* | 3/2012 | Caldwell ............ G01R 27/2605 |
| | | 327/517 |
| 2012/0113047 A1 | 5/2012 | Hanauer et al. |
| 2013/0069672 A1 | 3/2013 | Pedersen et al. |
| 2013/0155630 A1 | 6/2013 | Yilmaz et al. |
| 2015/0094974 A1 | 4/2015 | Backes |
| 2015/0130750 A1 | 5/2015 | Morrison |

FOREIGN PATENT DOCUMENTS

| | | |
|---|---|---|
| WO | 2010111362 A1 | 9/2010 |
| WO | 2013163496 A2 | 10/2013 |

\* cited by examiner

SIMULTANEOUS TIME DOMAIN DIFFERENTIAL SENSING AND ELECTRIC FIELD SENSING

CROSS-REFERENCE TO RELATED APPLICATIONS

This application is a continuation of U.S. application Ser. No. 17/401,144, filed on Aug. 12, 2021, U.S. application Ser. No. 17/401,144 is a continuation of U.S. application Ser. No. 15/122,541, filed on Aug. 16, 2016, U.S. application Ser. No. 15/122,541 claims priority to PCT Application No. PCT/US2015/018593, filed on Mar. 4, 2015, PCT Application No. PCT/US2015/018593 claims priority to U.S. Application No. 61/947,641, filed Mar. 4, 2014, the disclosures of which are incorporated by reference in their entirety.

BACKGROUND OF THE INVENTION

The present invention relates to systems and methods for detecting a touch input.

Touch inputs are widely used as an input methodology. For example, touch inputs are used in conjunction with appliances, tablets, and smartphones. Touch inputs can be determined based on a capacitive output of an electrode. According to one known method, the value of the capacitive output is used to determine the presence of a touch input on a substrate or the location of a touch input on a two-dimensional panel.

FIG. 1 illustrates a known circuit for detecting a touch input using self-capacitance. The circuit includes a measurement circuit and a signal processing circuit. The measurement circuit includes a voltage source (Vdd), electrodes for eight capacitive buttons (Ce1, Ce2 . . . Ce8), and a sampling capacitor (Cs). Each electrode is independently sampled. The output of each electrode is forwarded to the signal processing circuit. The signal processing circuit includes an amplifier, an analog-to-digital converter, and a time domain differential signature processing circuit. The signal processing circuit includes an output response, for example a digital signal indicative of the time of a touch input at one of the eight capacitive buttons.

FIG. 2 illustrates another known circuit for detecting a touch input using mutual-capacitance. The circuit of FIG. 2 includes the signal processing circuit of FIG. 1, however the measurement circuit is modified to include an electrode pairing for each of the eight capacitive buttons. The voltage source (Vdd) provides a stimulus voltage to sequential ones of the electrode pairings. The output of each electrode pairing is forwarded to the signal processing circuit. The signal processing circuit amplifies each output before converting each output into a digital signal for time domain differential processing. The output response includes a digital signal indicative of the time of a touch input at one of the eight capacitive buttons.

The circuits of FIGS. 1-2 digitally process each electrode output sampled by the measurement circuit. This scheme is potentially burdensome, particularly if rapid measurements are required for the time domain differential processing circuit. Accordingly, there remains a continued need for circuits and methods that rapidly measure electrode capacitance while minimizing computing resources, optionally for use in conjunction with time domain differential processing methods.

SUMMARY OF THE INVENTION

Systems and methods for determining a touch input are provided. The systems and methods generally include measuring the peak voltage at an electrode over a measurement period and determining a touch input based on that peak voltage. The systems and methods can conserve computing resources by deferring digital signal processing until after a peak electrode capacitance has been sampled. The systems and methods are suitable for capacitive sensors using self-capacitance and capacitive sensors using mutual capacitance. The systems and methods are also suitable for capacitive buttons, track pads, and touch screens, among other implementations.

According to one embodiment, the system includes a capacitive sensor for receiving a touch input. The capacitive sensor includes a driver circuit, a measurement circuit, and a signal processing circuit. The driver circuit is adapted to providing a stimulus voltage, for example a repeating square wave, to a capacitive coupling. The measurement circuit includes a peak detector and provides an output proportional to the peak voltage across the capacitive coupling over a measurement period. The signal processing circuit is then adapted to process the peak voltage in digital logic to determine the presence or absence of a touch input on a touch substrate of the capacitive sensor.

According to another embodiment, the measurement circuit includes a strobe electrode and a sense electrode defining a capacitive coupling therebetween, the capacitive coupling being adapted to vary in response to a touch input. The driver circuit is adapted to provide a repeating stimulus voltage to the strobe electrode over a measurement period. The measurement circuit includes a peak detector electrically coupled to the sense electrode. The peak detector is adapted to measure the peak voltage over the same measurement period for output to a signal processing circuit.

According to still another embodiment, the measurement circuit includes a plurality of electrode pairs, each including a strobe electrode and a sense electrode, and a corresponding plurality of peak detectors. The measurement circuit is adapted to simultaneously sample the peak voltage for each of the electrode pairs, and to subsequently forward the peak voltage for the desired electrode pair to the signal processing circuit. The signal processing circuit optionally includes a time domain differential processing circuit to determine the rate of change of the output of the measurement circuit, which can then be used to determine the presence of a touch input.

According to yet another embodiment, the measurement circuit includes a single strobe electrode and a plurality of sense electrodes. The strobe electrode is capacitively coupled to the plurality of sense electrodes to define a plurality of capacitive couplings. The measurement circuit additionally includes a peak detector for each of the sense electrodes, the peak detectors being adapted to simultaneously sample the peak voltage for each capacitive coupling over a measurement period. The measurement circuit is further adapted to forward the peak voltage for the desired capacitive coupling to the signal processing circuit. The signal processing circuit optionally includes a time domain differential processing circuit to determine the rate of change of the output of the measurement circuit, which can then be used to determine the presence of a touch input.

According to even another embodiment, the signal processing circuit detects a touch input by determining the rate of change of electrode capacitance. The rate of change of electrode capacitance can decrease, slowing to nearly zero, as an object comes to rest against a touch surface. As the rate of change of electrode capacitance falls below a threshold value, a touch condition is registered. The touch condition can correspond to the object coming to rest, or very nearly to rest, for example the placement and flattening of a fingertip against a touch substrate. The signal processing circuit can additionally include an amplifier coupled to the output of the measurement circuit and an analog-to-digital converter coupled to the output of the amplifier.

These and other features and advantages of the present invention will become apparent from the following description of the invention, when viewed in accordance with the accompanying drawings and appended claims.

DESCRIPTION OF THE CURRENT EMBODIMENTS

The current embodiments generally relate to systems and methods for determining a touch input. The systems and methods generally include measuring the peak voltage at an electrode over a measurement period and determining a touch input based on the peak voltage. The systems and methods can conserve computing resources by deferring digital signal processing until after a peak voltage has been measured. The systems and methods are suitable for capacitive sensors using self-capacitance and capacitive sensors using mutual capacitance. The systems and methods are also suitable for capacitive buttons, track pads, and touch screens, among other implementations. In addition, the systems and methods can be implemented in conjunction with the sensing circuits set forth in WO2010/111362 to Caldwell et al entitled "Apparatus and Method for Determining a Touch Input," and WO2013/163496 to Caldwell et al entitled "Apparatus and Method for Determining a Stimulus, Including a Touch Input and a Stylus Input," the disclosures of which are incorporated by reference in their entirety.

Figure 1:
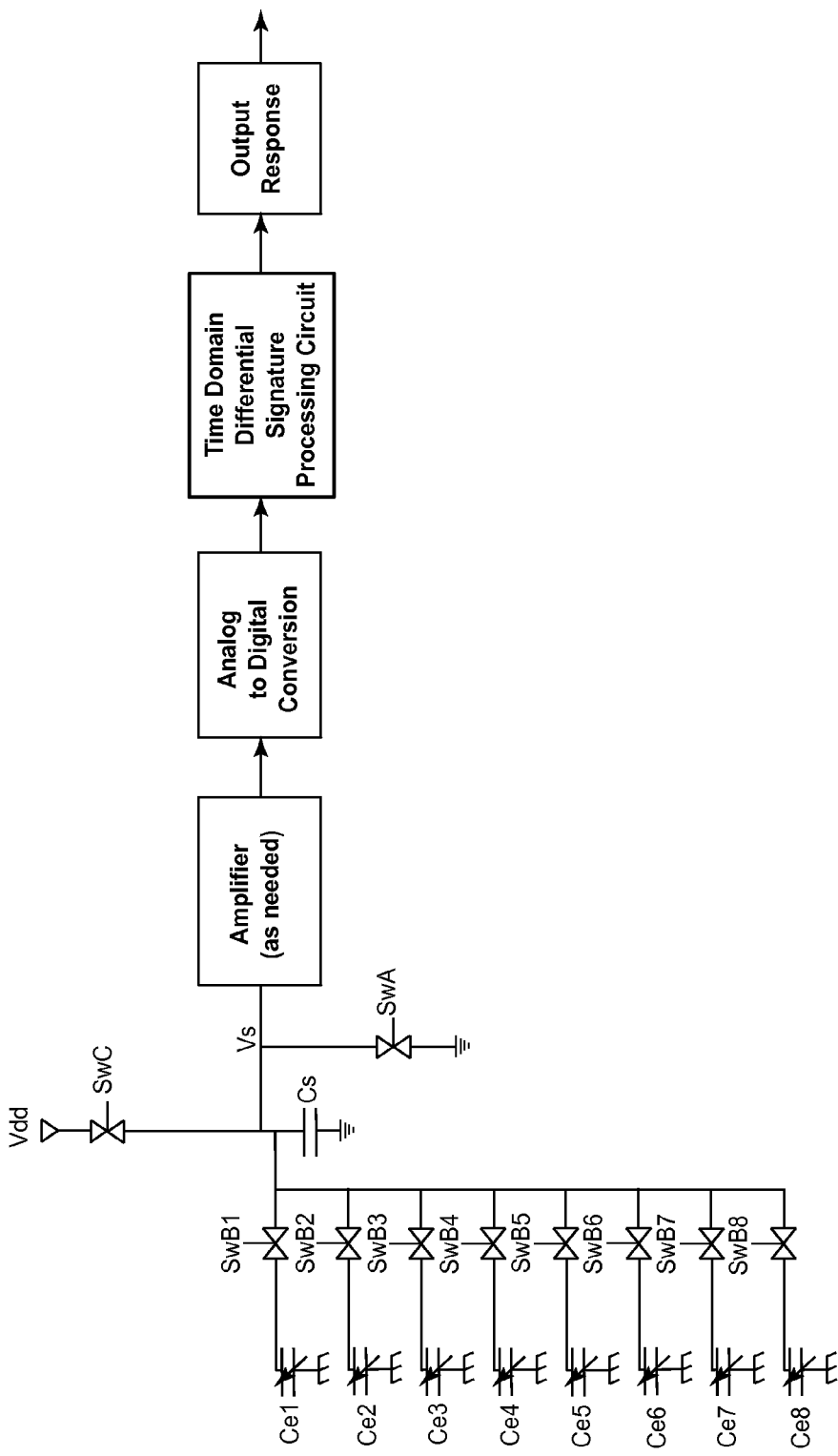
FIG. 1 is a circuit diagram of a prior art capacitive touch sensor including eight capacitive buttons using self-capacitance.
Figure 2:
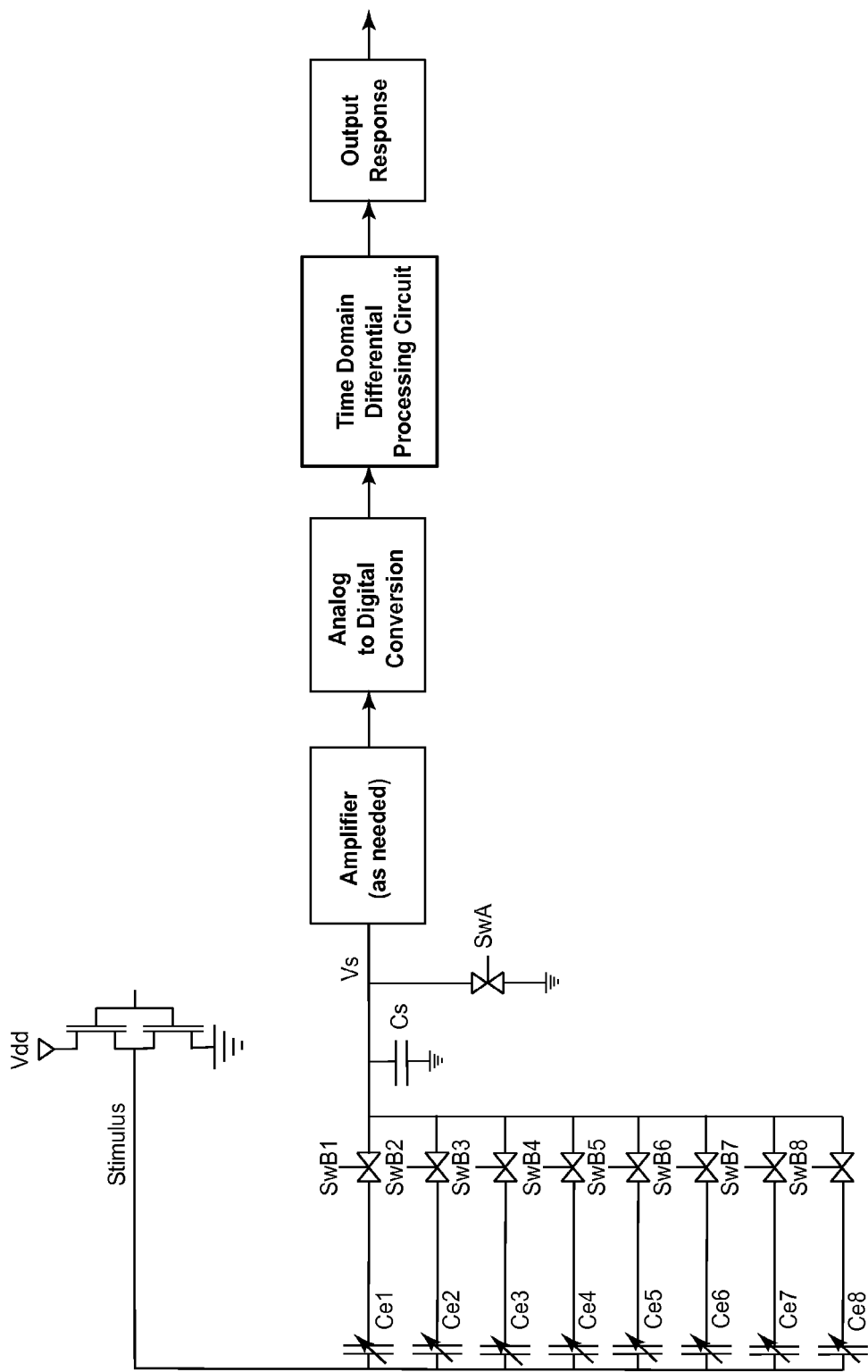
FIG. 2 is a circuit diagram of a prior art capacitive touch sensor including eight capacitive buttons using mutual-capacitance.
Figure 3:
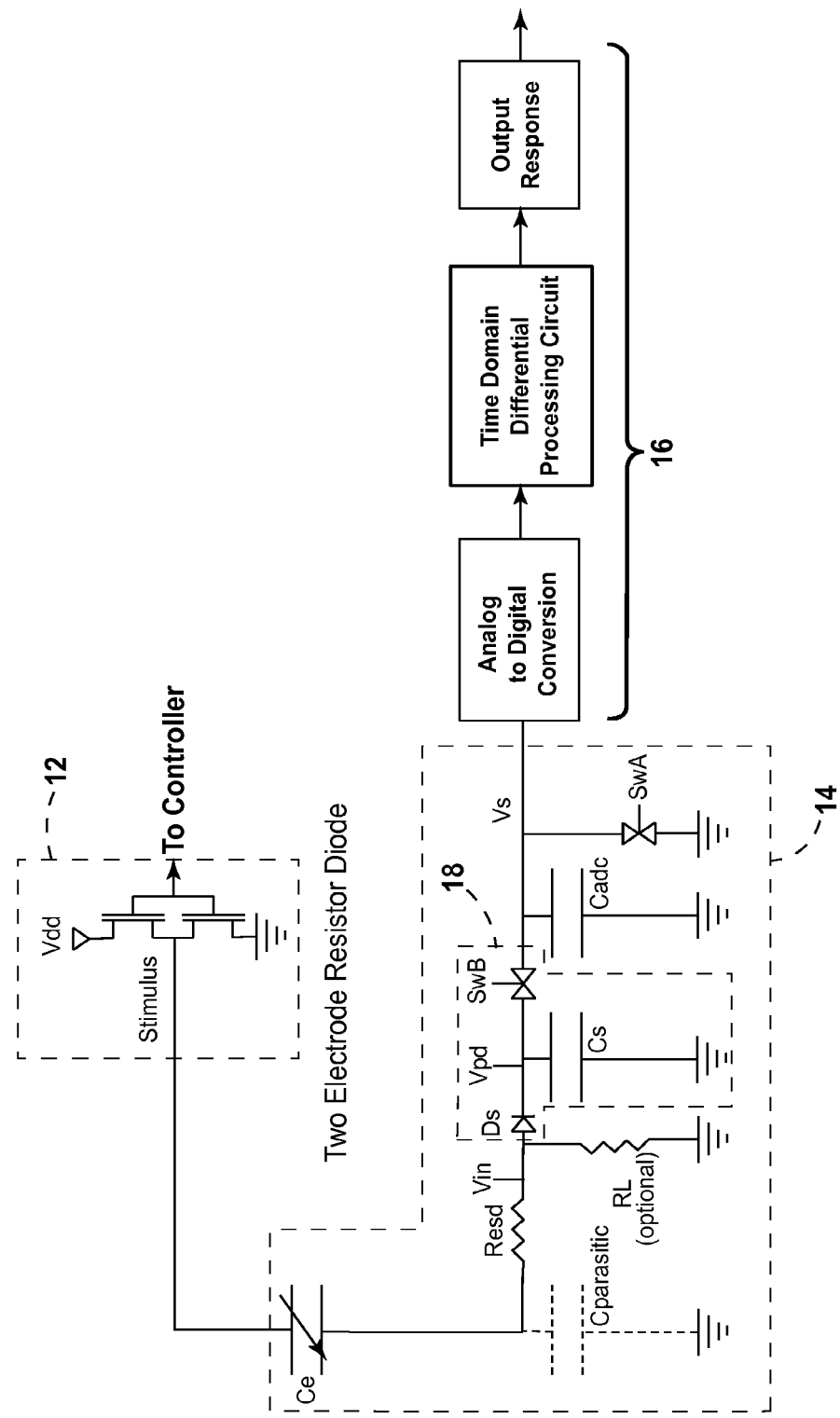
FIG. 3 is a circuit diagram of a capacitive touch sensor in accordance with a first embodiment.

Referring now to FIG. 3, a circuit diagram for a capacitive sensor in accordance with a first embodiment is illustrated. The capacitive sensor includes a driving circuit 12, a measurement circuit 14, and a signal processing circuit 16. The driving circuit 12 includes a voltage source (Vdd) that is adapted to provide a stimulus voltage, for example the repeating 3V square shown in FIG. 4. The voltage source is optionally controlled by a controller, for example an ASIC, an FPGA, or a microcontroller, which also controls operation of the switches in FIG. 3. The measurement circuit 14 additionally includes a measurement capacitor (Ce), and in particular a strobe electrode capacitively coupled to a sense electrode. The measurement capacitor (Ce) includes a capacitance that changes depending on the presence or absence of touch input on a nearby touch substrate. For example, when "no touch" is present, the measurement capacitor (Ce) may have a lower value of capacitance than when a "touch" is present. Likewise, when a "touch" is present, the measurement capacitor (Ce) may have a higher value of capacitance.

Figure 4:
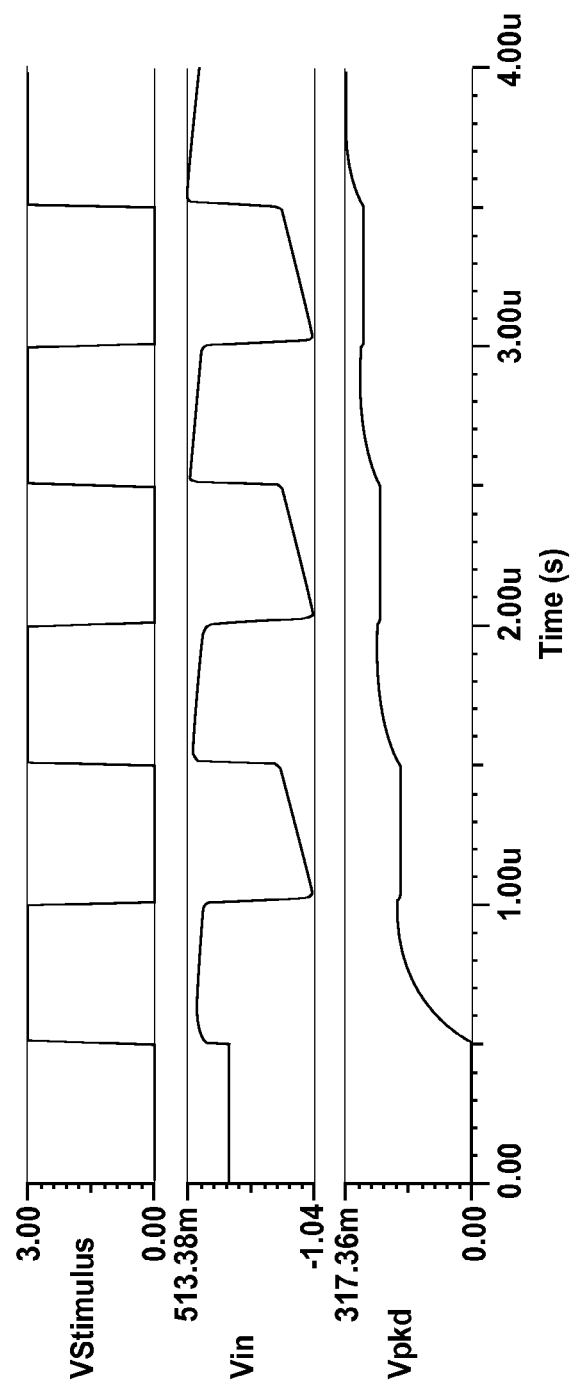
FIG. 4 is a first timing diagram of the capacitive touch sensor of FIG. 3.

The measurement circuit 14 additionally includes a peak detector 18. The peak detector 18 is adapted to output a DC voltage proportional to the peak value of the AC voltage across the measurement capacitor (Ce). The peak detector 18 includes a peak detector diode (Ds), a peak detector capacitor (Cs), and a gate switch (SwB), the diode (Ds) and the capacitor (Cs) being connected in series to ground. The diode (Ds) conducts positive half cycles, charging the capacitor (Cs) to the waveform peak. When the input waveform falls below the DC peak stored to the capacitor (Cs), the diode (Ds) is reverse biased, blocking current flow from the capacitor (Cs) to the capacitor (Ce). Thus, the capacitor (Cs) retains the peak value even when the waveform drops to zero. Stated somewhat differently, the peak detector 18 generally includes an analog memory, for example the capacitor (Cs), to store a charge proportional to the peak value of the voltage across the measurement capacitor (Ce). The peak detector 18 additionally includes a unidirectional switch, for example the diode (Ds), to charge the capacitor (Cs) when a new peak arrives at the input of the peak detector. The peak detector 18 additionally includes a switch to periodically reinitialize the output to zero, for example the gate switch (SwB), at the end of the measurement cycle. As further shown in FIG. 4, exemplary stimulus voltage (VStimulus) includes a repeating 3V square wave. The voltage across the capacitor (Vin) and the voltage at the peak detector capacitor (Vpkd) is also shown in FIG. 4. The voltage at the peak detector capacitor (Cs) can take several cycles to charge to the peak due to the series resistance (RC time constant).

Referring again to FIG. 3, the measurement circuit 14 includes an electrostatic suppression resistor (Resd) and a load resistor (RL) to discharge parasitic capacitance. The load resister (RL) may be used to provide a lower impedance path or to attenuate the output from the driving circuit 12, such that the waveform can be attenuated prior to detecting a peak voltage at the peak detector capacitor (Cs). The measurement circuit additionally includes a sample-and-hold capacitor (Cadc) and a discharge switch (SwA). The gate switch (SwB) and the discharge switch (SwA) are operatively coupled to the same controller that controls operation of the voltage source (Vdd). When the gate switch (SwB) is closed and the discharge switch (SwA) is open, the DC output of the peak detector 18 is provided to the signal processing circuit 16. When the gate switch (SwB) is open and the discharge switch (SwA) is closed, the sample-and-hold capacitor (Cadc) is discharged to ground for the subsequent measurement cycle. Each measurement cycle can include two or more cycles of the repeating waveform, such that the peak voltage is selected from among at least two available 'peaks' of an AC signal. The measurement cycle can include 10 microseconds in some embodiments, such that a peak voltage is provided to the signal processing circuit 16 every 10 microseconds. The measurement cycle can include other durations in other embodiments where desired.

The signal processing circuit 16 includes an analog-to-digital converter (ADC), a Time Domain Differential Processing Circuit, and an Output Response. The ADC converts the analog DC output of the measurement circuit 14 into a digital signal for processing by the Time Domain Differential Processing Circuit. The Time Domain Differential Processing Circuit can perform the processing steps set forth in WO2010/111362 to Caldwell et al entitled "Apparatus and Method for Determining a Touch Input," and WO2013/163496 to Caldwell et al entitled "Apparatus and Method for Determining a Stimulus, Including a Touch Input and a Stylus Input." The processing steps are generally programmed into computer readable memory that, when executed, cause a processor to determine the presence or absence of a stimulus, for example a touch input or a touch signature. The instructions that are performed by the processor are generally stored in a computer readable data storage device. The computer readable data storage device can be a portable memory device that is readable by the computer apparatus. Such portable memory devices can include a compact disk, a digital video disk, a flash drive, and any other disk readable by a disk driver embedded or externally connected to a computer, a memory stick, or any other portable storage medium whether now known or hereinafter developed. Alternatively, the machine-readable data storage device can be an embedded component of a computer such as a hard disk or a flash drive of a computer. Together, the computer and machine-readable data storage device can be a standalone device or embedded into a machine or a system that uses the instructions for a useful result. The Output Response can include a digital signal indicative of the timing of a touch input on a touch substrate. Further by example, the digital signal can include the touch signature, including for example the duration of the touch input, the rate at which the finger or stylus approached the touch substrate, and the rate at which the finger or stylus receded from the touch substrate. Other characteristics of the touch signature may be included in the Output Response in other embodiments where desired.

Figure 5:
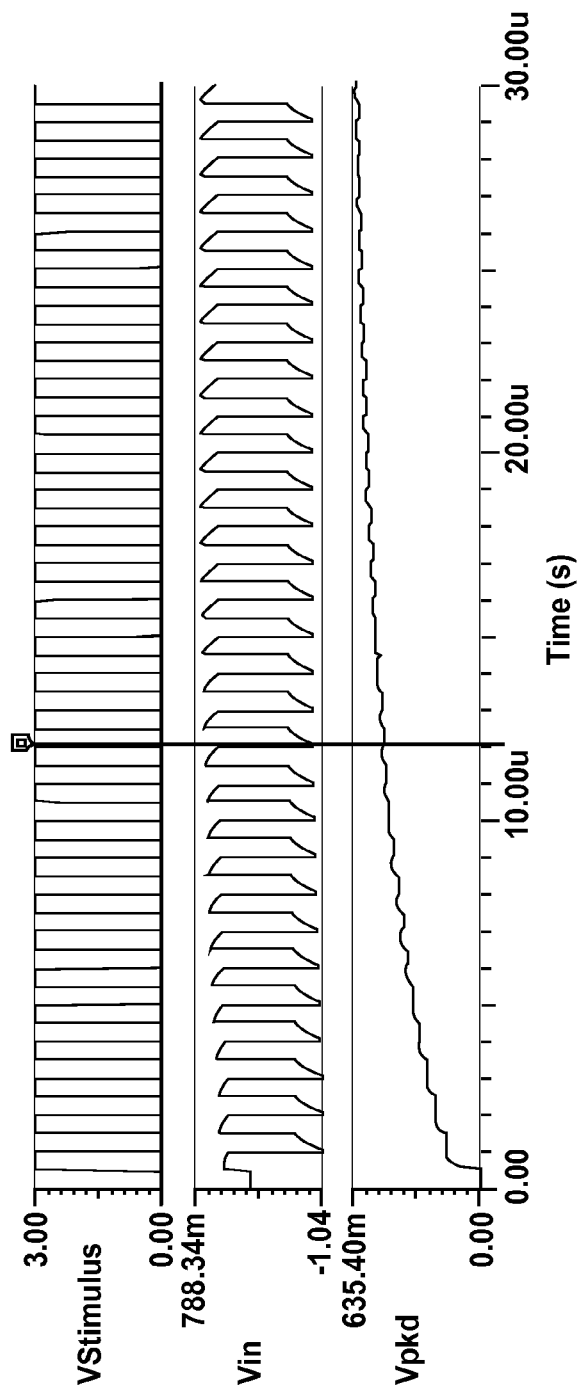
FIG. 5 is a second timing diagram of the capacitive touch sensor of FIG. 3.
Figure 6:
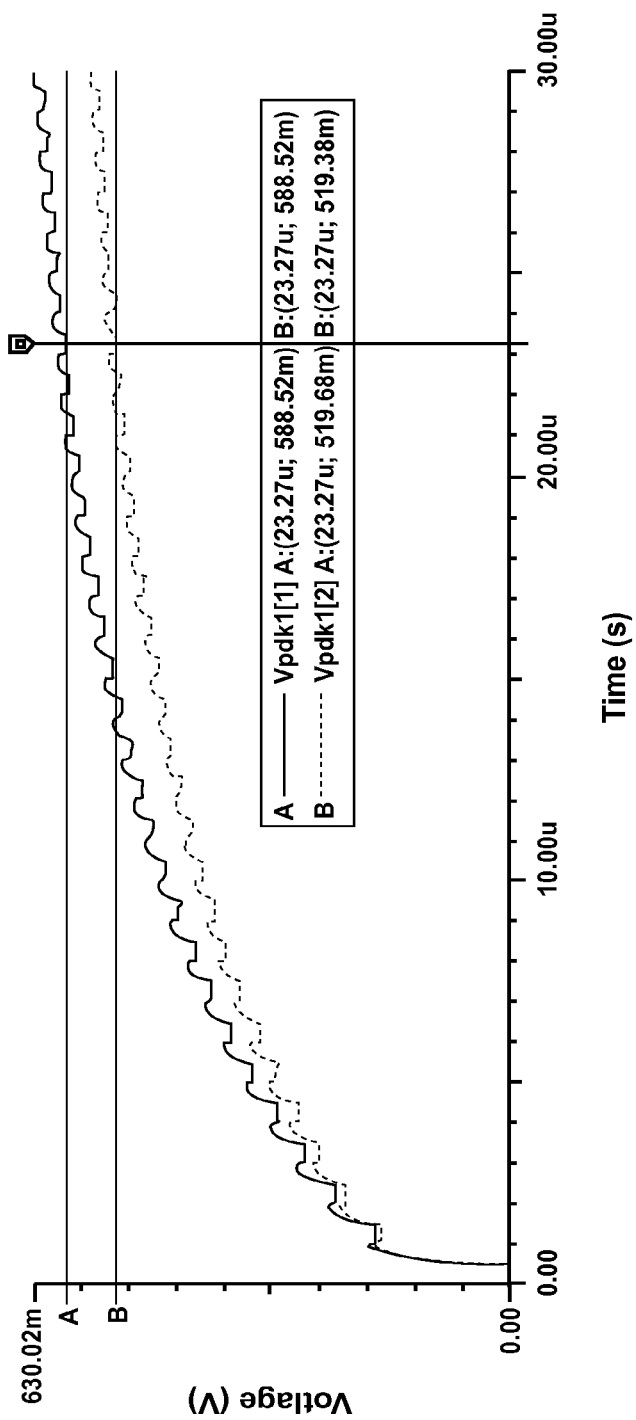
FIG. 6 is a third timing diagram of the capacitive touch sensor of FIG. 3.

Referring now to FIGS. 5 and 6, multiple samples may be made at a faster rate to increase signal fidelity and to reduce noise. By increasing the frequency of the AC stimulus voltage, signal to noise ratio is increased, the response time is decreased (due to a faster sampling rate that is not limited by an ADC conversion time), resulting in a decreased power draw (less digital processing and ADC operation). An amplifier may be added to the signal processing circuit 16, which can further decrease the response time (less ADC samples to achieve an increased signal level) and decrease power draw (less digital processing and ADC operation provided amplifier is a low power amplifier).

In the interest of clarity, the general outline of the driving circuit 12, the measurement circuit 14, and the signal processing circuit 16 are not reproduced in the embodiments of FIGS. 7-49, but are nevertheless present in those drawings.

Figure 7:
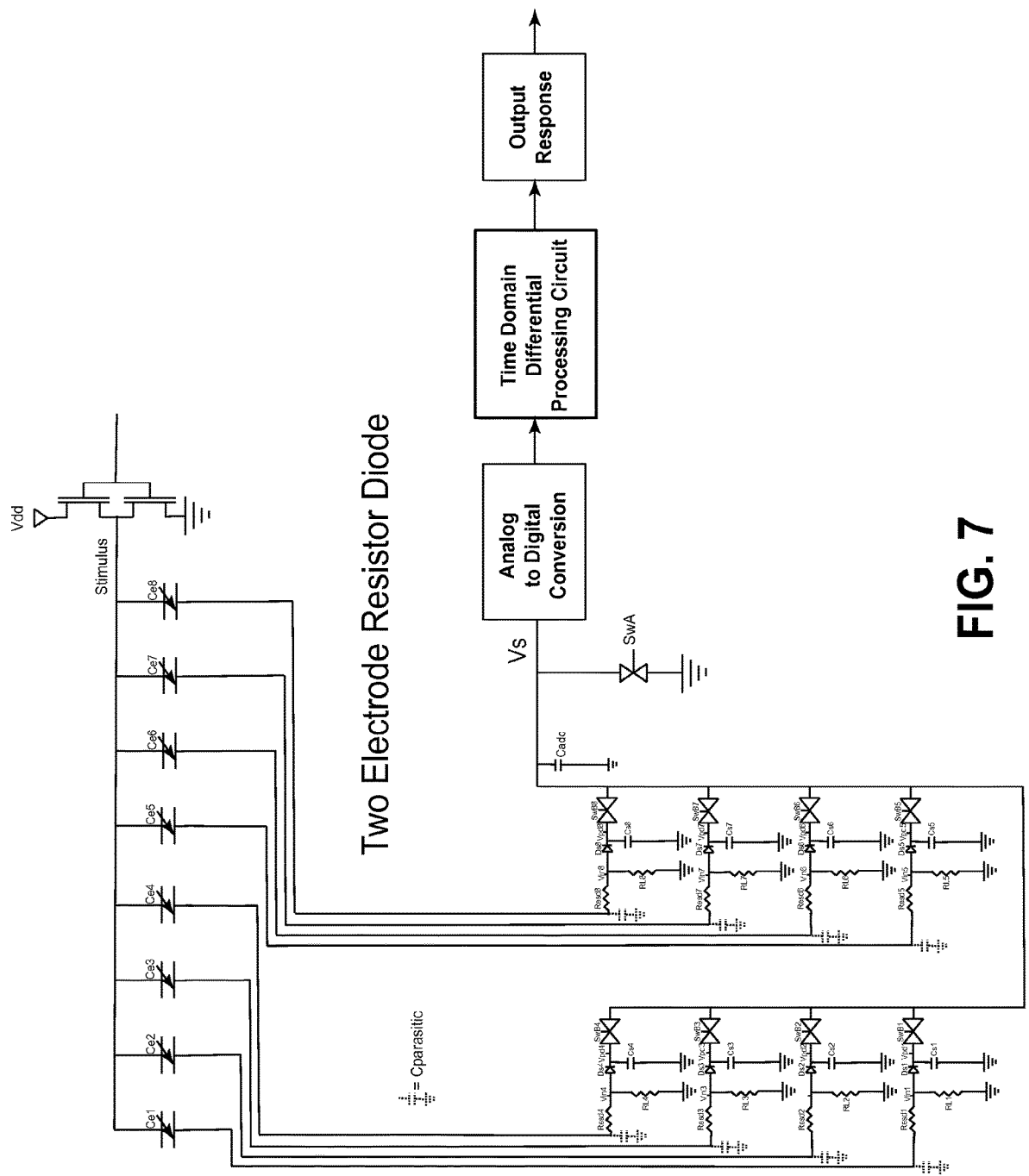
FIG. 7 is a circuit diagram of a capacitive touch sensor in accordance with a second embodiment.
Figure 46:
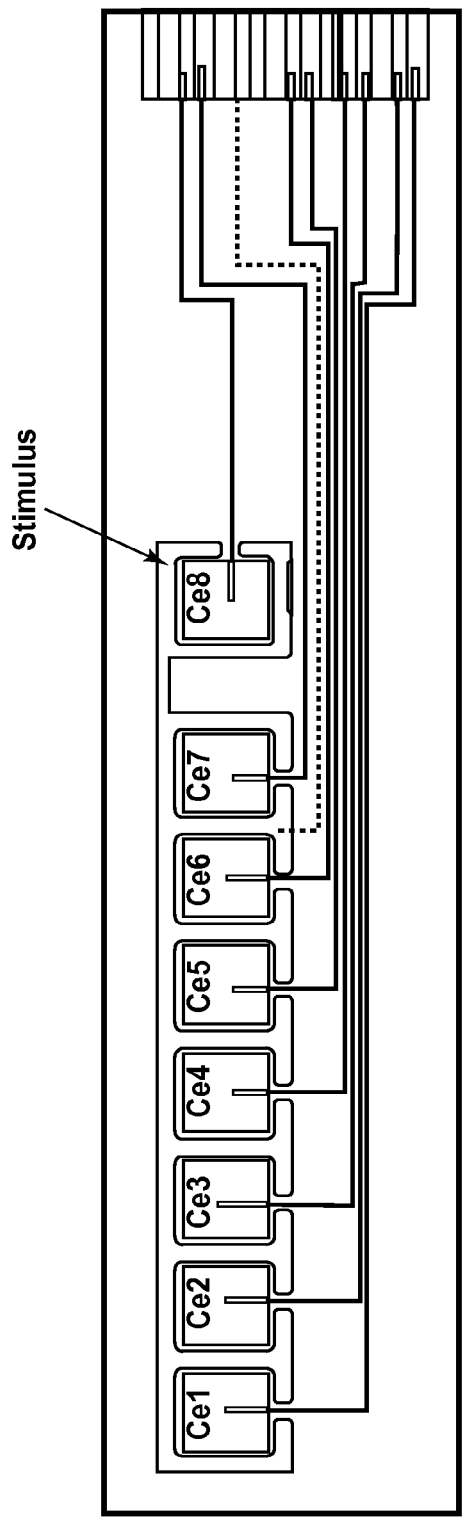
FIG. 46 is a depiction of eight dual-electrodes for use with the foregoing embodiments using mutual-capacitance.

Referring to FIG. 7, a circuit diagram for a capacitive sensor in accordance with a second embodiment is illustrated. The capacitive sensor of FIG. 7 is similar in structure and function as the capacitive sensor of FIG. 3, except that the capacitive sensor of FIG. 7 includes a plurality of measurement capacitors (Ce1, Ce2 . . . Ce8) and a corresponding plurality of peak detectors. The peak detectors include a diode (Ds1, Ds2 . . . Ds8), a peak detector capacitor (Cs1, Cs2 . . . Cs8), and a gate switch (SwB1, SwB2 . . . SwB8). The peak detectors are connected through the gate switch (SwB1, SwB2 . . . SwB8) to the sample-and-hold capacitor (Cadc). The measurement circuit 14 can additionally include an electrostatic suppression resistor (Resd1, Resd2 . . . Resd8) and a load resistor (RL1, RL2 . . . RL3) for each measurement capacitor (Ce1, Ce2 . . . Ce8). In this embodiment, the measurement capacitor (Ce1, Ce2 . . . Ce8) includes a single strobe electrode and eight sense electrodes. An exemplary physical construction is depicted in FIG. 46, where the strobe electrode is depicted as "Stimulus" and the sense electrodes are depicted as Ce1, Ce2 . . . Ce8. The driving circuit 12 can simultaneously stimulate each of the measurement capacitors (Ce1, Ce2 . . . Ce8) over the same measurement cycle. The discharge switch (SwA) is used to couple the DC output of a selected one of the peak detector capacitors (Cs1, Cs2 . . . Cs8) with the ADC of the signal processing circuit 16. The signal processing circuit 16 then determines which, if any, of the measurement capacitors (Ce1, Ce2 . . . Ce8) registered a touch input during the measurement cycle. If the measurement cycle is kept sufficiently small, the signal processing circuit 16 effectively determines the presence of simultaneous touch inputs using a single time domain differential processing circuit, rather than a dedicated circuit for each measurement capacitor (Ce1, Ce2 . . . Ce8).

Figure 8:
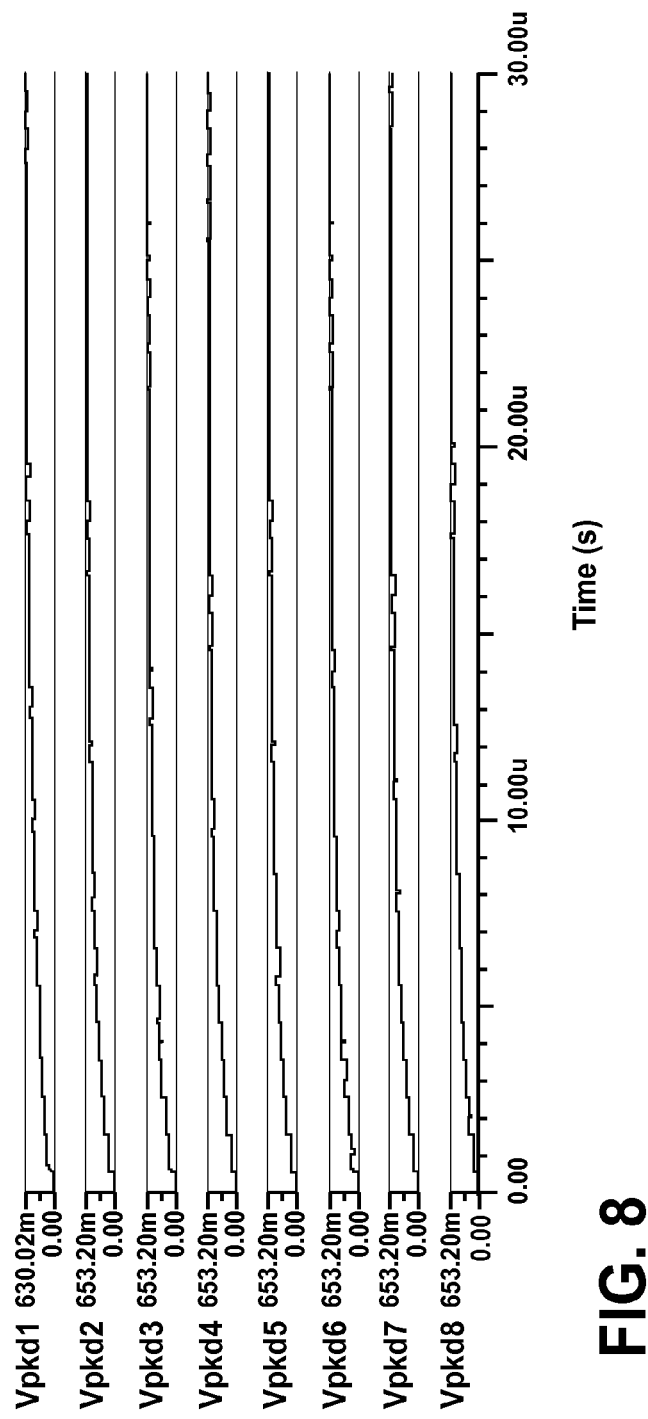
FIG. 8 is a timing diagram of the capacitive touch sensor of FIG. 7.

Referring now to FIG. 8, multiple samples may be made at a faster rate to increase signal fidelity and to reduce noise. By increasing the frequency of the AC stimulus voltage, signal to noise ratio is increased, the response time is decreased (due to a faster sampling rate that is not limited by an ADC conversion time), and the power draw is decreased (less digital processing and ADC operation). An amplifier may be added to the signal processing circuit 16, which can further decrease the response time (less ADC samples to achieve an increased signal level) and decrease power draw (less digital processing and ADC operation provided amplifier is a low power amplifier). Noise will tend to cancel due to the simultaneous measurements of common mode noise.

Figure 9:
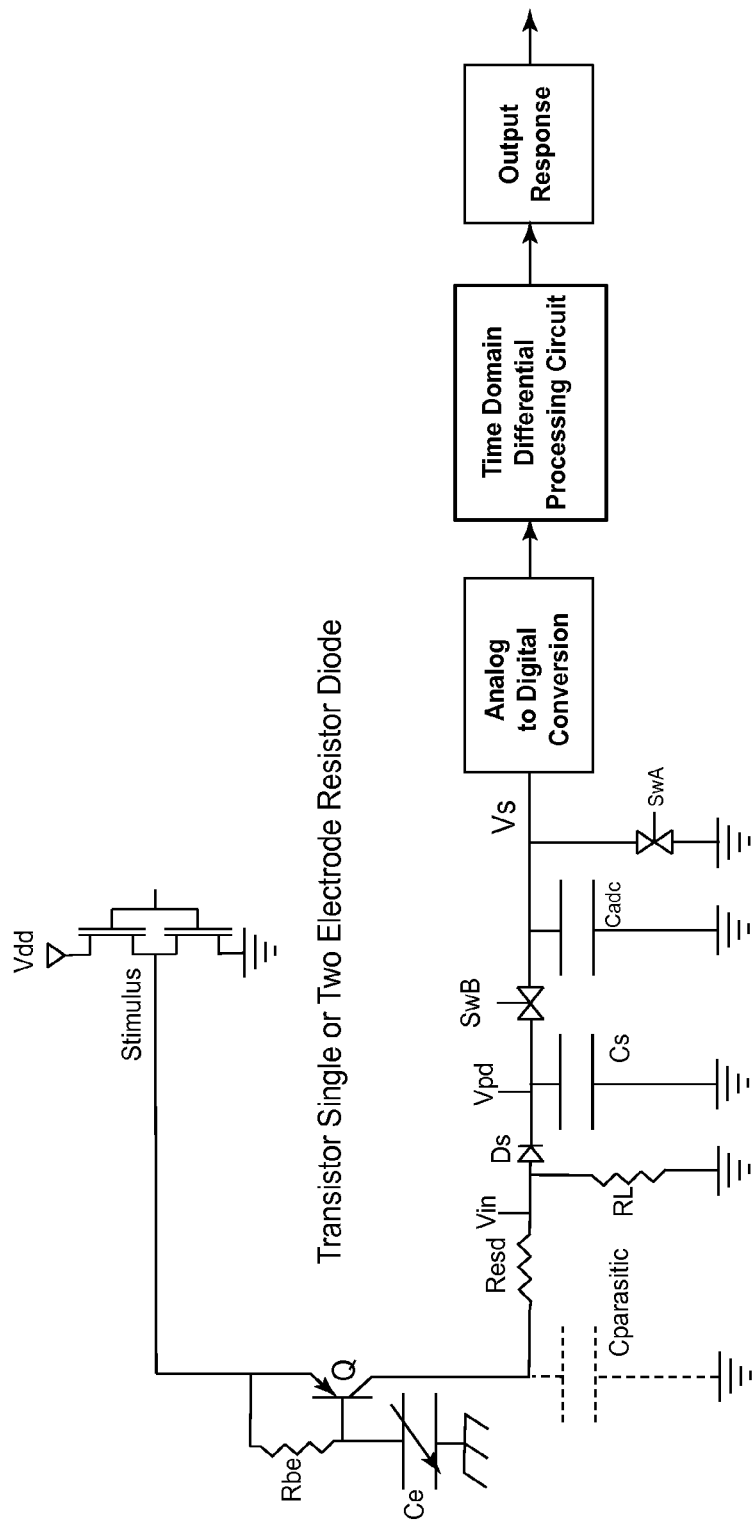
FIG. 9 is a circuit diagram of a capacitive touch sensor in accordance with a third embodiment.
Figure 10:
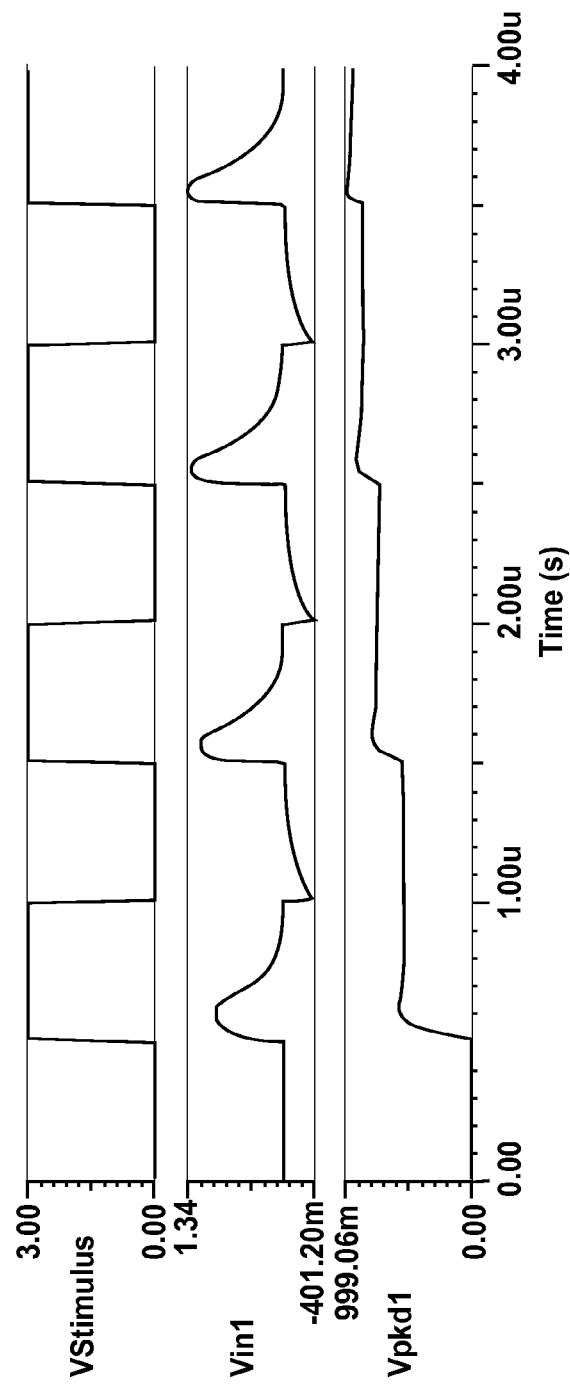
FIG. 10 is a first timing diagram of the capacitive touch sensor of FIG. 9.
Figure 11:
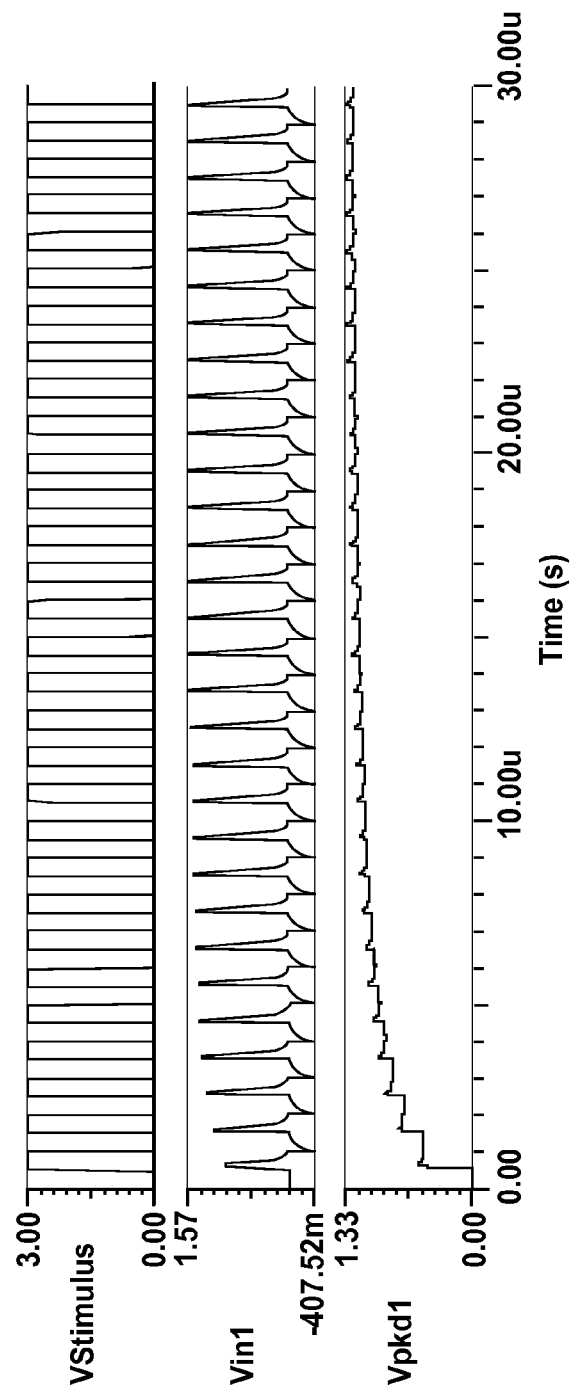
FIG. 11 is a second timing diagram of the capacitive touch sensor of FIG. 9.
Figure 12:
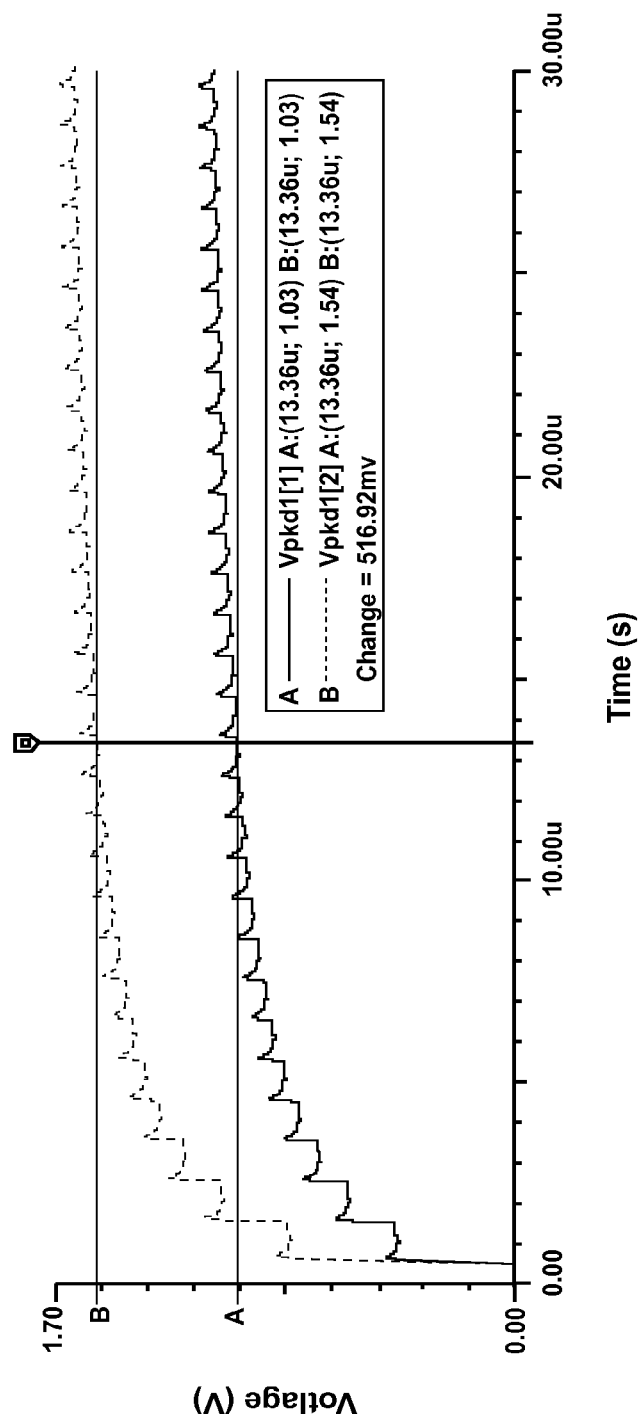
FIG. 12 is a third timing diagram of the capacitive touch sensor of FIG. 9.

Referring to FIG. 9, a circuit diagram for a capacitive sensor in accordance with a second embodiment is illustrated. The capacitive sensor of FIG. 9 is similar in structure and function as the capacitive sensor of FIG. 3, except that the measurement capacitor (Ce) includes a transistor-controlled electrode for measuring self-capacitance. In particular, a PNP transistor (Q) includes an emitter that is coupled to the voltage source (Vdd), a base coupled to a resistor (Rbe), and a collector coupled to the peak detector diode (Ds). In operation, the measurement electrode (Ce) and the resistor (Rbe) form a delay network. For example, the stimulus voltage causes a voltage to develop between the emitter and the base of the PNP transistor (Q), causing a base current to flow. This will in turn cause collector current to flow that is proportional to the gain of the transistor (Q). If the capacitance of the measurement capacitor (Ce) increases due to a stimuli, for example a touch input, the collector current will increase, which will charge the peak detector capacitor (Cs) for a give pulse of stimulus. FIG. 10 includes a timing diagram illustrating operation of the capacitive sensor of FIG. 9. The voltage (Vin) immediately prior to the peak detector diode (Ds) rises and falls with the stimulus voltage (VStimulus) during the measurement cycle, accompanied by the charging of the peak detector capacitor (Cs). FIG. 11 includes the results of repeated pulses of sampling. After the measurement cycle, all capacitors including parasitic capacitance are discharged and the process is repeated for processing by the Time Domain Differential Processing Circuit, after possible amplification and analog-to-digital conversion. FIG. 12 also shows the increased response time and sensitivity attributed to the transistor (Q).

Figure 13:
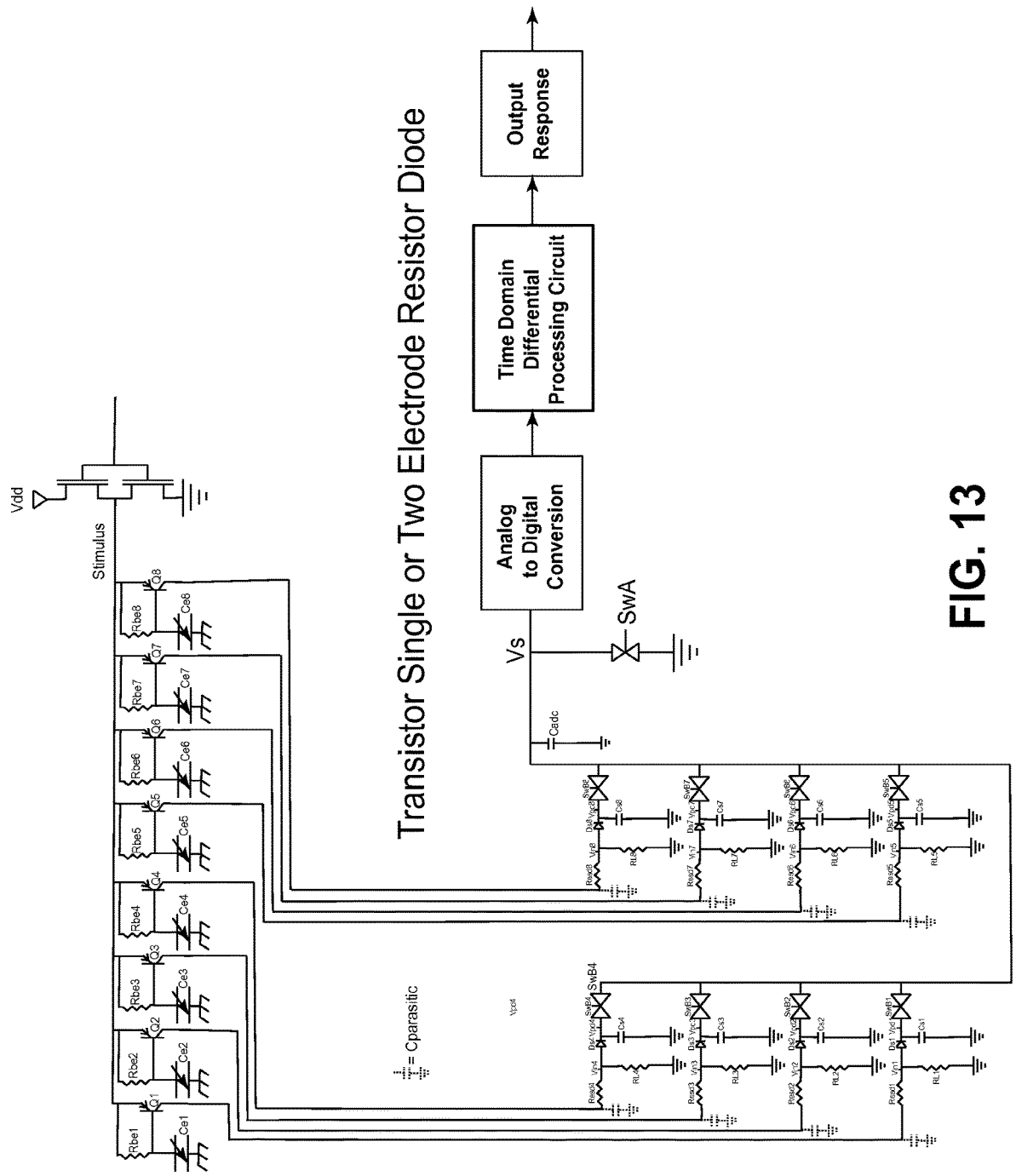
FIG. 13 is a circuit diagram of a capacitive touch sensor in accordance with a fourth embodiment.
Figure 14:
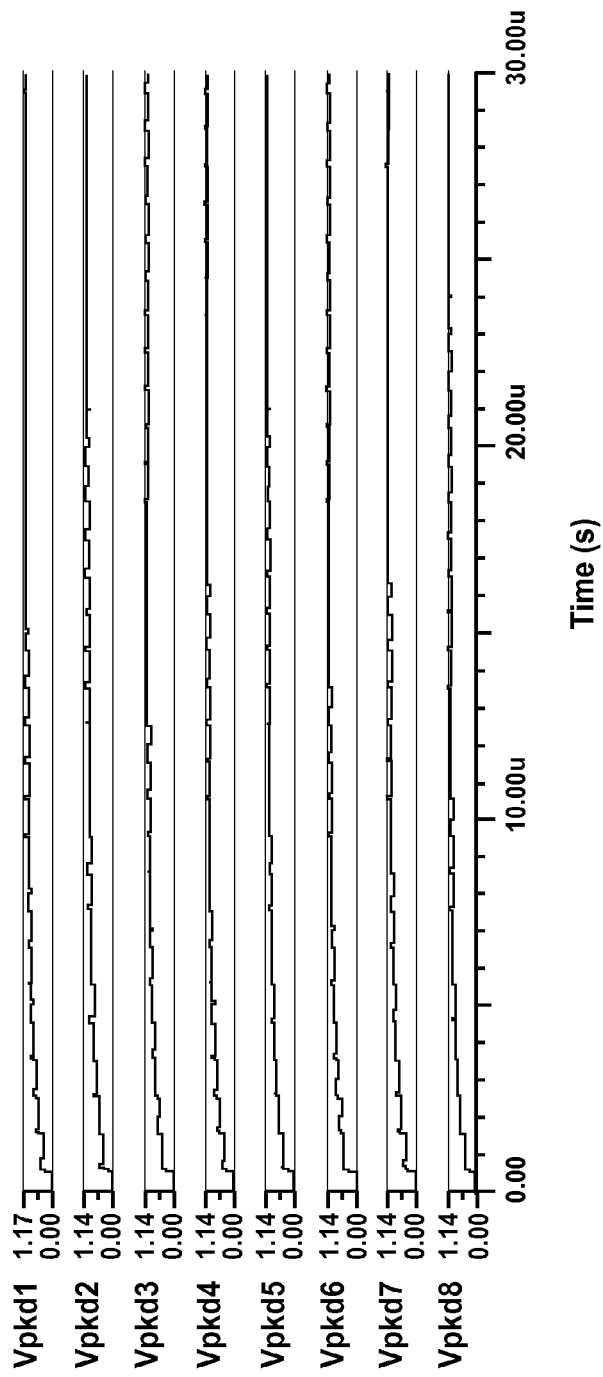
FIG. 14 is a timing diagram of the capacitive touch sensor of FIG. 13.

Referring to FIG. 13, a circuit diagram for a capacitive sensor in accordance with a fourth embodiment is illustrated. The capacitive sensor of FIG. 13 is similar in structure and function as the capacitive sensor of FIG. 9, except that the capacitive sensor of FIG. 13 includes a plurality of measurement capacitors (Ce1, Ce2 . . . Ce8) and a corresponding plurality of peak detectors. Each measurement capacitor (Ce1, Ce2 . . . Ce8) is electrically coupled to a resistor (Rbe1, Rbe2 . . . Rbe8) and a PNP transistor (Q1, Q2 . . . Q8), such that the measurement capacitor (Ce1, Ce2 . . . Ce8) and the resistors (Rbe1, Rbe2 . . . Rbe8) form a delay network across the transistors (Q1, Q2 . . . Q8). Each transistor collector is coupled to a peak detector, and in particular a peak detector diode (Ds1, Ds2 . . . Ds8) and a peak detector capacitor (Cs1, Cs2 . . . Cs8). The peak detector capacitors (Cs1, Cs2 . . . Cs8) are connected through a gate switch (SwB1, SwB2 . . . SwB8) to the sample and hold capacitor (Cadc). The measurement circuit 14 can additionally include an electrostatic suppression resistor (Resd1, Resd2 . . . Resd8) and a load resistor (RL1, RL2 . . . RL3) for each measurement capacitor (Ce1, Ce2 . . . Ce8). In this embodiment, the measurement capacitor (Ce1, Ce2 . . . Ce8) includes a single strobe electrode. The driving circuit 12 can simultaneously stimulate each of the strobe electrodes over the same measurement cycle. The discharge switch (SwA) is used to couple the DC output of a selected one of the peak detection capacitors (Cs1, Cs2 . . . Cs8) with the ADC of the signal processing circuit 16. The signal processing circuit 16 then determines which, if any, of the peak detector capacitors (Cs1, Cs2 . . . Cs8) registered a touch input during the measurement cycle. FIG. 11 includes the results of repeated pulses of sampling. If the measurement cycle is kept sufficiently small, the signal processing circuit 16 effectively determines the presence of simultaneous touch inputs using a single time domain differential processing circuit, rather than a dedicated circuit for each peak detector capacitor (Cs1, Cs2 . . . Cs8). After the measurement cycle, all capacitors (including parasitic capacitance) are discharged and the process is repeated for processing by the Time Domain Differential Processing Circuit, after possible amplification and analog-to-digital conversion.

Figure 15:
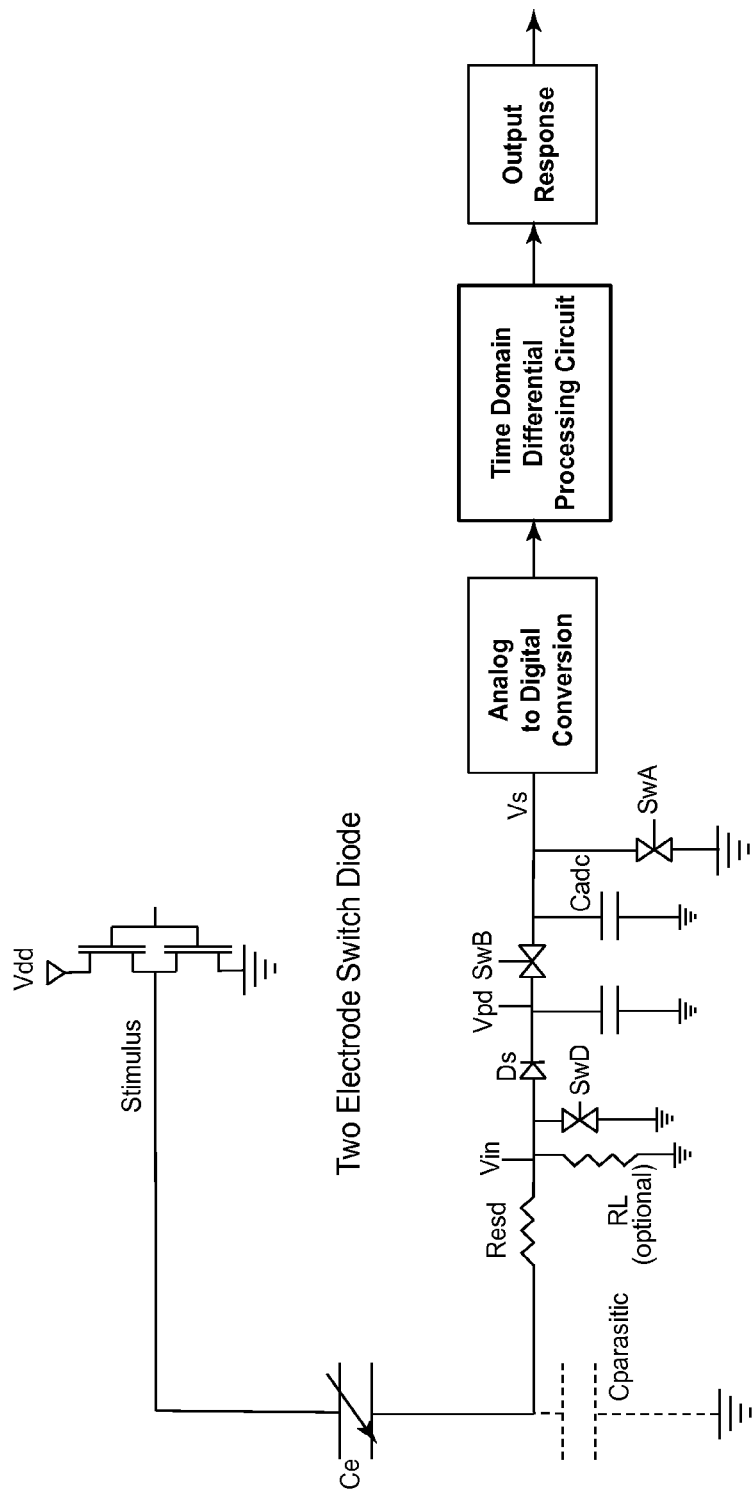
FIG. 15 is a circuit diagram of a capacitive touch sensor in accordance with a fifth embodiment.
Figure 16:
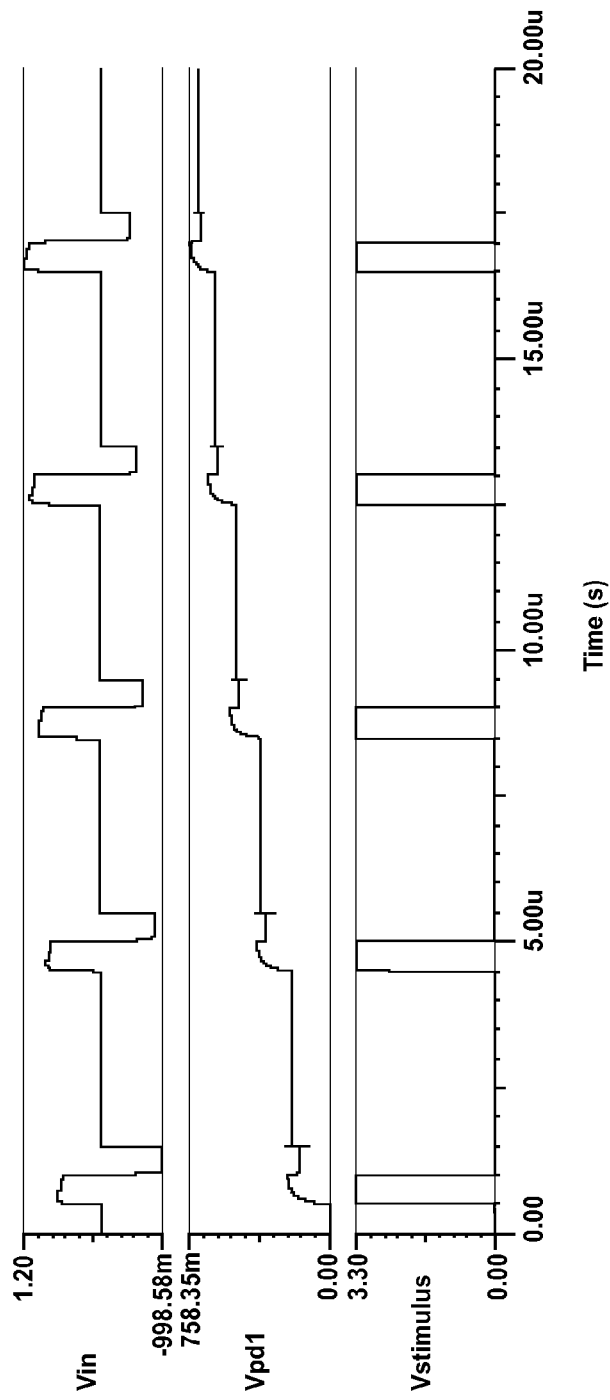
FIG. 16 is a first timing diagram of the capacitive touch sensor of FIG. 15.
Figure 17:
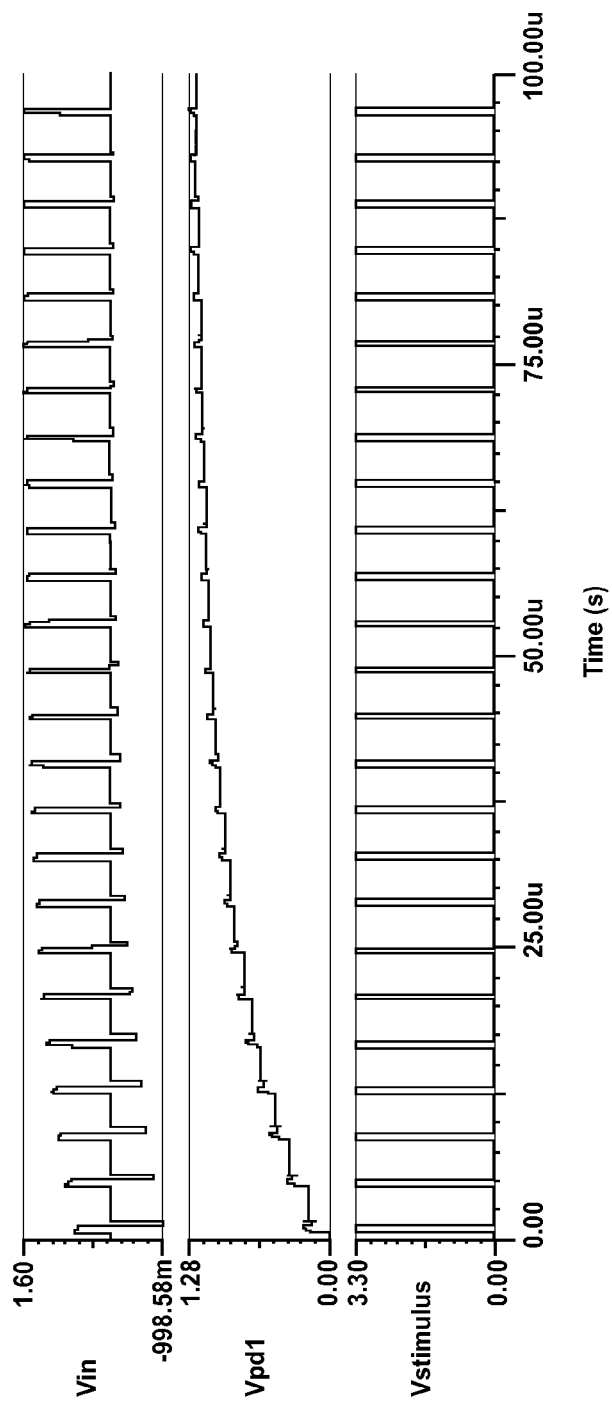
FIG. 17 is a second timing diagram of the capacitive touch sensor of FIG. 15.
Figure 18:
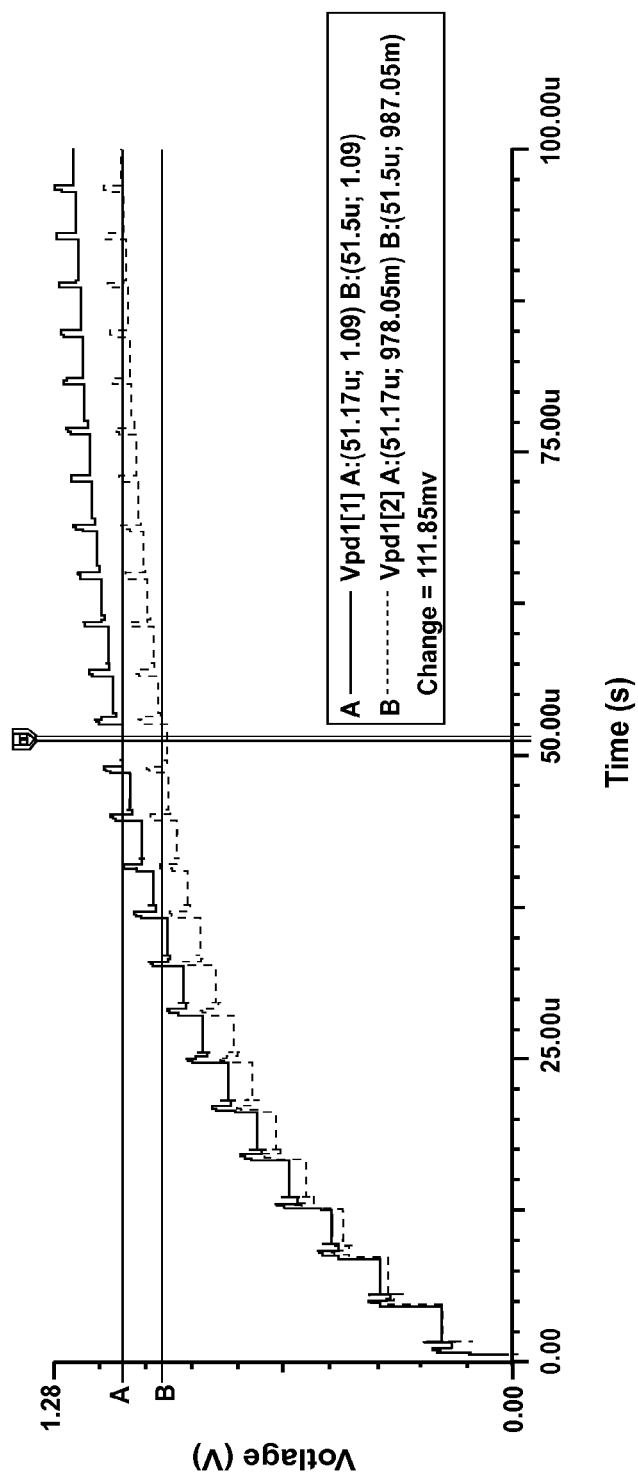
FIG. 18 is a third timing diagram of the capacitive touch sensor of FIG. 15.

FIG. 15 illustrates an electrical schematic and block diagram of a capacitance sensor in accordance with a fifth embodiment. Timing diagrams associated with one or more operational states of the illustrated embodiment are shown in FIGS. 16 through 18. The sensor is similar to the sensor described in connection with the illustrated embodiment of FIG. 3, but with several differences. The sensor of FIG. 15 includes a measurement circuit 14 configured to assess multiple samples generated by the driving circuit 12, and to provide an output indicative of a characteristic of the multiple samples, such as a peak voltage detected across a capacitive coupling over a measurement period. The characteristic can be unique among the multiple samples generated over the measurement period, or can be based on one or more aspects of several of the multiple samples.

In the illustrated embodiment, the capacitive touch sensor of FIG. 15 may include driver circuitry 12 and signal processing circuitry 16, similar to the driver circuitry 12 and signal process circuitry 16 of FIG. 3. And, similar to the sensor of FIG. 3, the basic technique utilized by the capacitive touch sensor for detecting and processing a touch input includes sensing the effective net capacitance of a capacitor. For example, the measurement capacitor (Ce), including a strobe electrode and a sense electrode, may represent the effective net capacitance of a single electrode sensing element. The effective capacitance seen by the sense electrode of the measurement capacitor (Ce) may change depending on the capacitance present, which further depends on whether a touch is present. In other words, when "no touch" is present, the measurement capacitor (Ce) may have a lower value of capacitance than when a "touch" is present. Likewise, when a "touch" is present, measurement capacitor (Ce) may have a higher value of capacitance. As discussed herein, the measurement circuitry 14 may assess the capacitance seen by the sense electrode over multiple samples, and provide an output indicative of a characteristic of the multiple samples, such as a peak voltage detected. The signal process circuitry 16 may evaluate the output from the measurement circuitry 14 to determine whether the output is indicative of a "touch" being present.

The measurement circuitry 14 of the illustrated embodiment of FIG. 15 includes a peak detector that detects a peak voltage of multiple samples of the measurement capacitor (Ce) generated by the driver circuitry. The peak detector may include a peak detector capacitor (Cs) and a peak detector diode (Ds). It should be understood that, as mentioned herein, the measurement circuitry may be constructed differently and may assess multiple samples in a different manner, such as by detecting a characteristic of the multiple samples other than the peak voltage. Similar to the measurement circuitry of FIG. 3, the measurement circuitry of FIG. 15 may include an electrostatic suppression resistor (Resd), an A-to-D gate switch (SwB), a sample/hold capacitor (Cadc), and a discharge switch (SwA). As discussed herein, and depicted in the illustrated embodiment of FIG. 15, parasitic capacitance may be present on the strobe electrode, potentially adversely affecting the ability of the measurement circuitry to assess effective capacitance seen by the strobe electrode. Adverse effects caused by the presence of parasitic capacitance may impact the samples generated by the drive circuitry, and skew or distort the output generated by the measurement circuitry, potentially causing a false positive indication or a false negative indication of a touch being present.

Adverse effects due to presence of parasitic capacitance may be reduced or eliminated using one or more of the configurations described herein. For example, in the illustrated embodiment of FIG. 3, the load resistor (RL) may be used to discharge parasitic capacitance. The load resistor (RL), as discussed herein, may be used to provide a lower impedance path or to attenuate the output from the drive circuit (12) to the measurement circuit (14) such that the output or sensor signal can be attenuated prior to peak detecting an accumulation of charge on the peak detector capacitor (Cs).

In the illustrated embodiment of FIG. 15, a parasitic discharge switch (SwD) may be selectively activated to discharge parasitic capacitance. The controller can control activation of the discharge switch (SwD) so that discharge of parasitic capacitance can be conducted at select periods of time rather than constantly. Optionally, the discharge switch (SwD) may be used in conjunction with a load resistor (RL) to affect parasitic capacitance. In this optional configuration, the load resistor (RL) may be used in conjunction with the discharge switch (SwD) to provide for adjustment of lower impedances of the output from the drive circuitry 15-102, or to attenuate the output of the drive circuitry 12 prior to peak detecting an accumulation of charge, or both.

Figure 19:
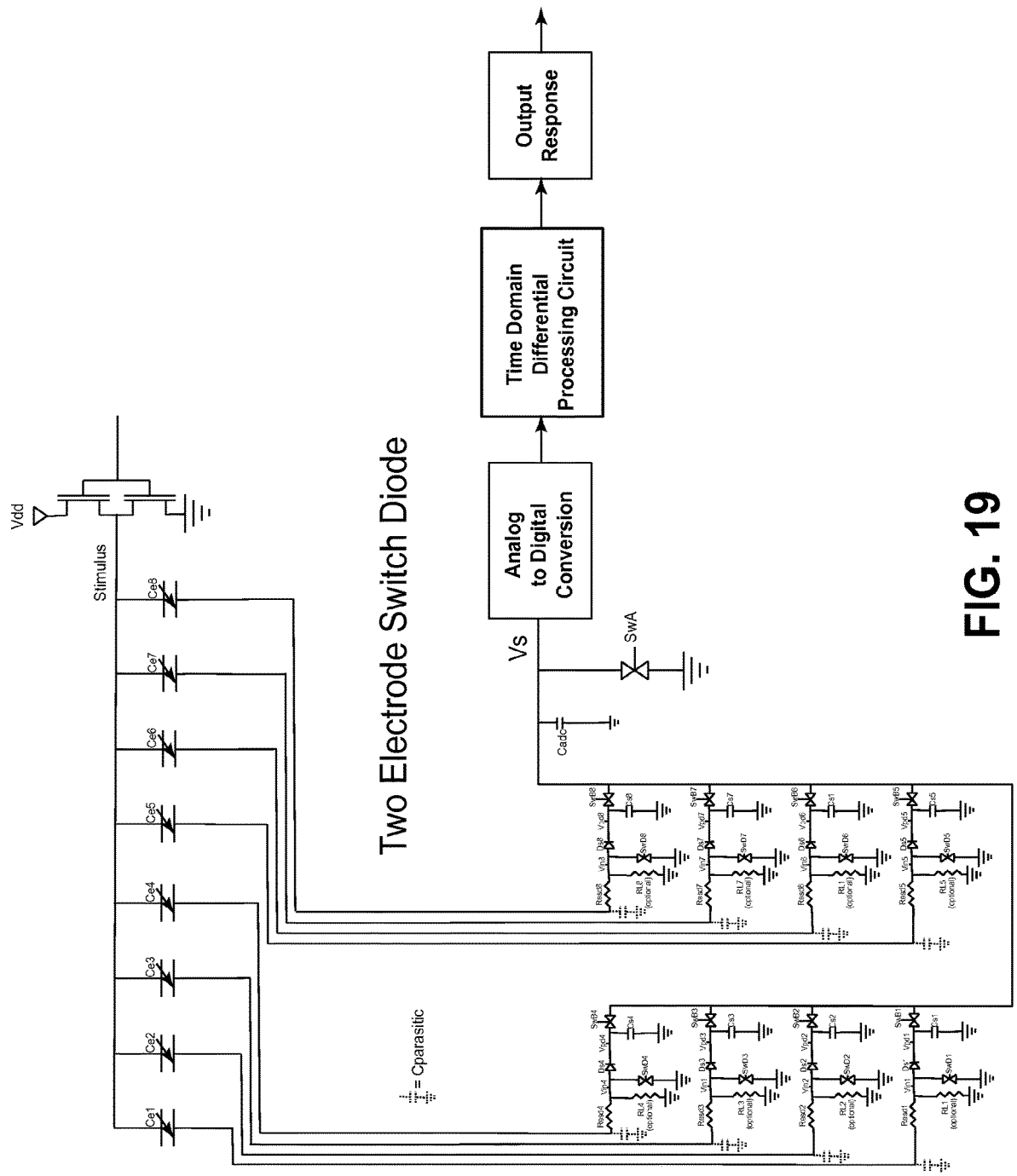
FIG. 19 is a circuit diagram of a capacitive touch sensor in accordance with a sixth embodiment.
Figure 20:
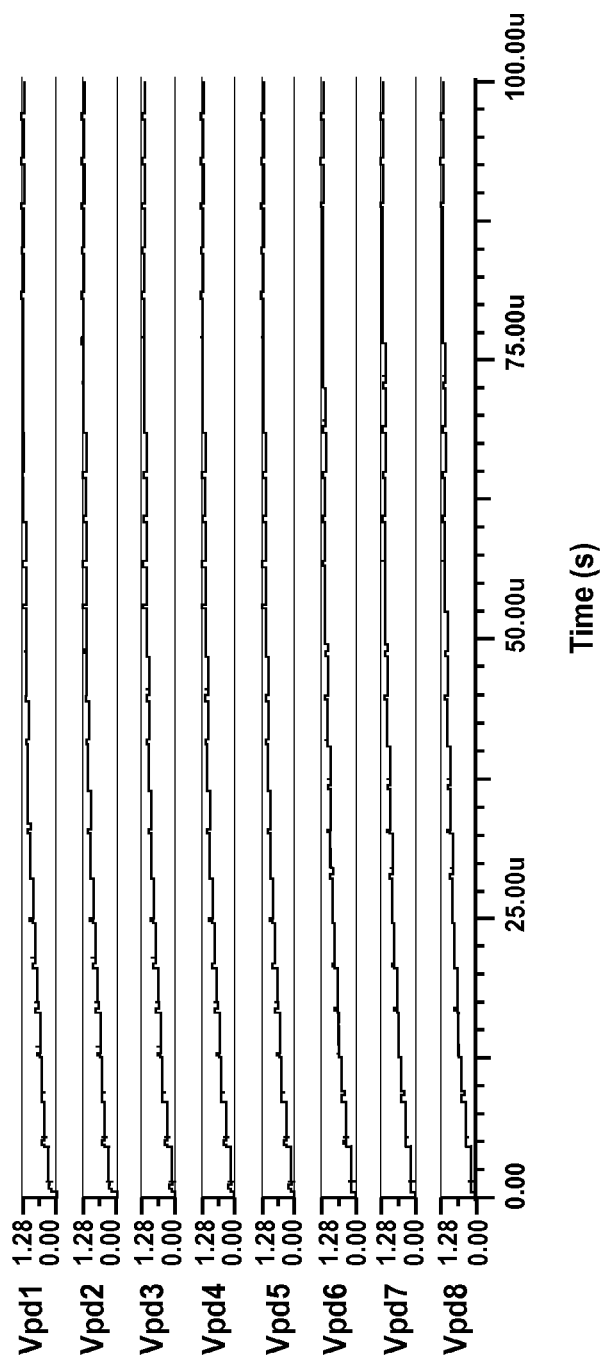
FIG. 20 is a timing diagram of the capacitive touch sensor of FIG. 19.

In the illustrated embodiment of FIG. 19, an electrical schematic and block diagram of a multi-electrode capacitance sensor or an array-type capacitance sensor is shown. A timing diagram associated with one or more operational states of the illustrated embodiment are shown in FIG. 20. With several exceptions, the capacitor touch sensor of FIG. 19 is similar to the capacitor touch sensor of FIG. 15. In particular, the capacitor touch sensor of FIG. 19 includes measurement circuitry that is configured to assess multiple samples generated by drive circuitry, and to provide an output indicative of the multiple samples to signal processing circuitry.

The multi-electrode capacitance sensor of FIG. 19 may operate in a manner generally similar to the multi-electrode capacitance sensor of FIG. 7. More specifically, the voltage source (Vdd) may stimulate multiple electrode sensing elements (Ce1, Ce2 . . . Ce8), similar to the measurement capacitor (Ce) described in connection with the illustrated embodiment of FIG. 15. Each of the multiple electrode sensing elements (Ce1, Ce2 . . . Ce8) may be incorporated into a respective measurement stage, which, similar to the measurement circuit, may assess the capacitance seen by a respective sensing element (Ce1, Ce2 . . . Ce8) over multiple samples generated by the voltage source (Vdd), and provide an output indicative of a characteristic of the multiple samples, such as a peak voltage detected. As used herein, a "measurement stage" includes the portion of the measurement circuit that detects the peak self-capacitance or the peak mutual capacitance over a measurement cycle for a given electrode or electrode pair. In the embodiment illustrated in FIG. 19, there are eight measurement stages, each corresponding to one of the measurement capacitors (Ce1, Ce2 . . . Ce8). Each of the measurement stages is configured to operate in the same manner; however, it should be understood that one or more measurement stages may be configured differently from another of the measurement stages. For example, one measurement stage may be configured as depicted in the illustrated embodiment, and another of the measurement stages may be configured according to another of the illustrated embodiments.

Each of the measurement stages may be selectively coupled to a sample/hold capacitor (Cadc), similar to the sample/hold capacitor (Cadc) in the illustrated embodiment of FIG. 15. For example, an output from a measurement stage may be selectively provided to the sample/hold capacitor (Cadc), while outputs from the remaining measurement stages are effectively disconnected from the sample/hold capacitor (Cadc). This configuration may prevent interference between measurement stages, and enable the signal processing circuitry to obtain an accurate measurement of each output provided to the sample/hold capacitor. Discharging of the sample/hold capacitor (Cadc) may be achieved via the discharge switch (SwA), similar to the discharge switch (SwA) in the illustrated embodiment of FIG. 15.

In the illustrated embodiment, the voltage source (Vdd) may generate multiple samples for each measurement electrode (Ce1, Ce2 ... Ce8), and for respective assessment by each of the measurement stages. The controller may control which output of the measurement stages is provided to the signal process circuitry, thereby enabling the signal process circuitry to evaluate the output and determine whether a "touch" is present in proximity to one or more of the electrode sensing element (Ce1, Ce2 ... Ce8).

Each of the measurement stages may operate in a manner similar to the measurement circuitry of the illustrated embodiment of FIG. 15. In other words, each of the measurement stages may include a peak detector including peak detector diode (Ds), a peak detector capacitor (Cs) and a gate switch (SwB). With this configuration, the diodes (Ds1, Ds2 ... Ds8) and the peak detector capacitors (Cs1, Cs2 ... Cs8) may assess multiple samples generated by the voltage source (Vdd) in order to identify a peak voltage of the multiple samples. This peak voltage may be supplied as an output of the measurement stage. It should be understood that each of the measurement stages may be configured differently according to one or more embodiments described herein.

Each of the measurement stages in the illustrated embodiment may include a discharge switch (SwD1, SwD2 ... SwD8), similar to the discharge switch (SwD) in the illustrated embodiment of FIG. 15, that is capable of discharging parasitic capacitance seen by the electrode sensing elements (Ce1, Ce2 ... Ce8). As discussed herein, adverse effects due to presence of parasitic capacitance may be reduced or eliminated using this configuration. Additionally, or alternatively, a load resistor (RL) may be included to discharge parasitic capacitance. Further, the load resistor (RL) may be used to provide a lower impedance path or to attenuate the output of the drive circuit.

Figure 21:
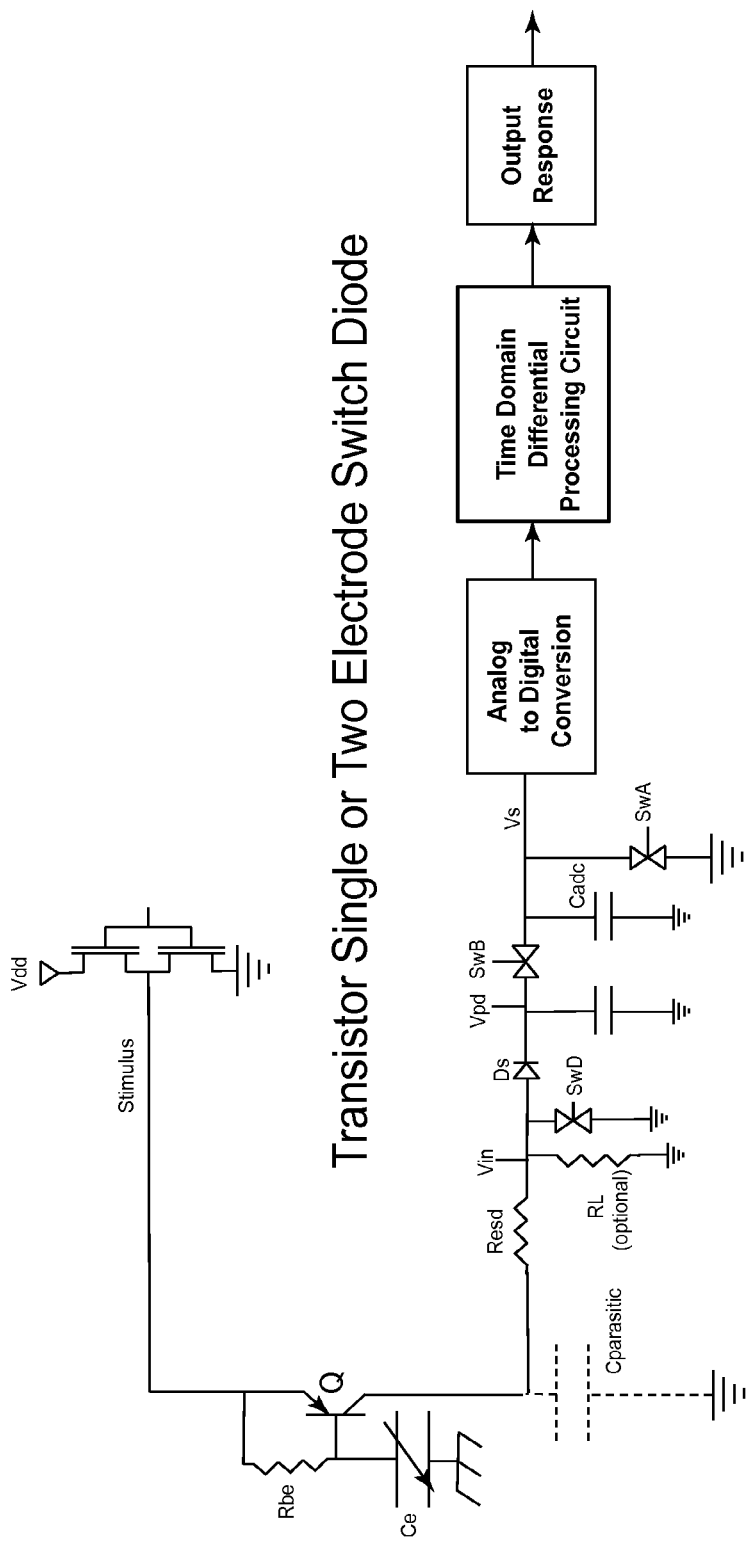
FIG. 21 is a circuit diagram of a capacitive touch sensor in accordance with a seventh embodiment.
Figure 22:
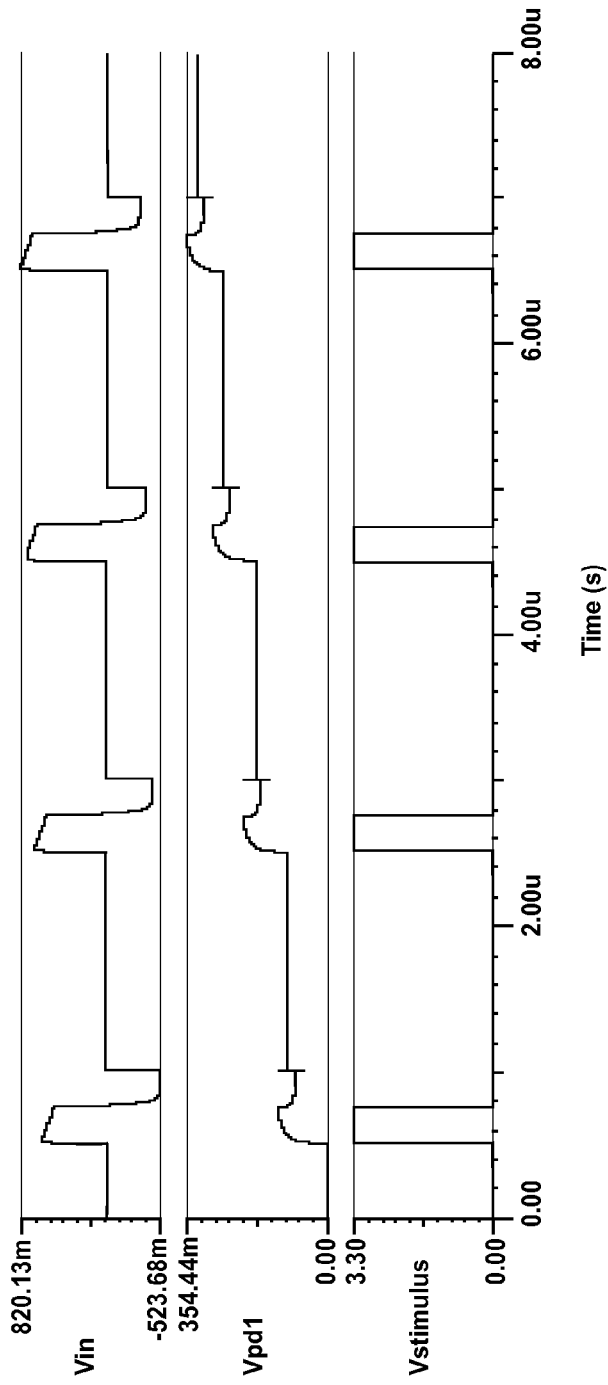
FIG. 22 is a first timing diagram of the capacitive touch sensor of FIG. 21.
Figure 23:
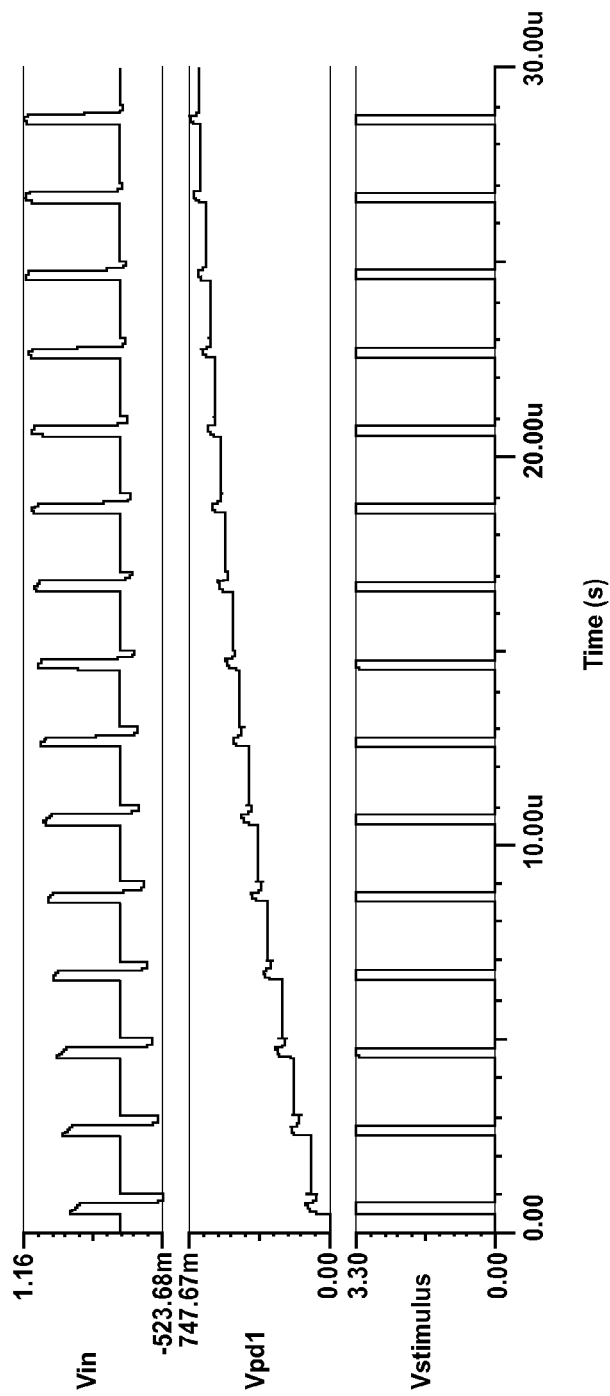
FIG. 23 is a second timing diagram of the capacitive touch sensor of FIG. 21.
Figure 24:
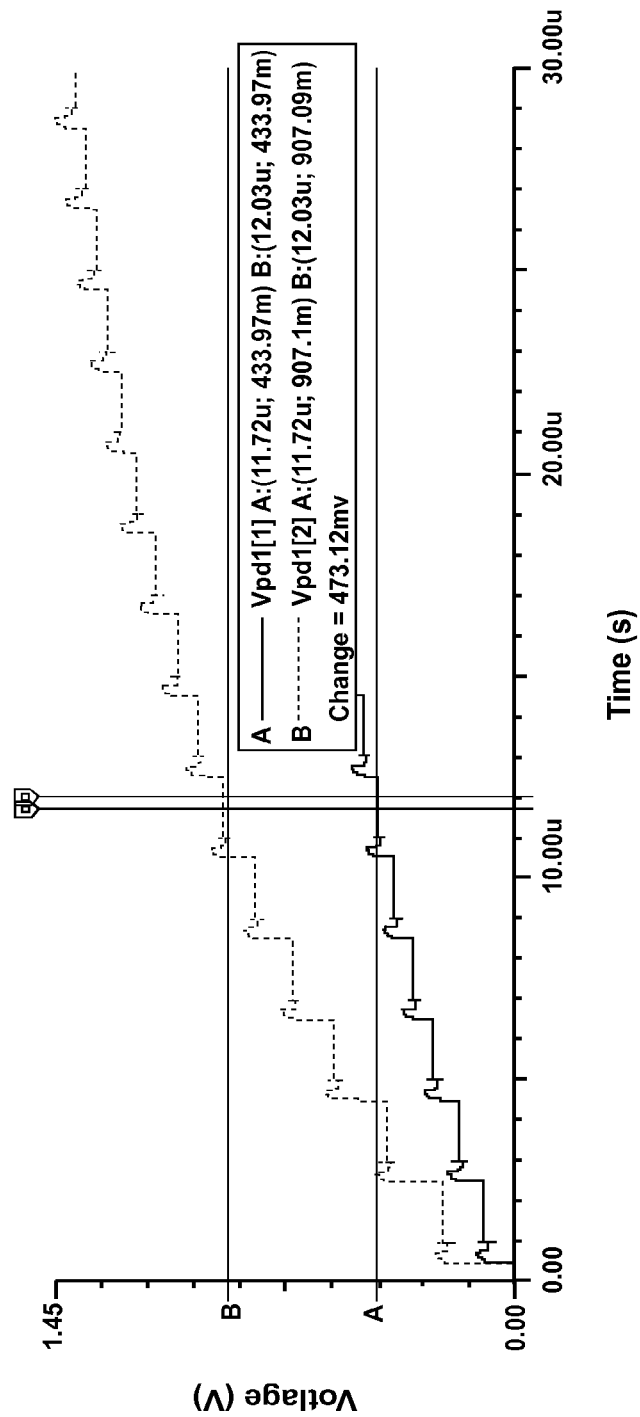
FIG. 24 is a third timing diagram of the capacitive touch sensor of FIG. 21.

FIG. 21 illustrates an electrical schematic and block diagram of a capacitive touch sensor in accordance with a seventh embodiment. Timing diagrams associated with one or more operational states of the illustrated embodiment are shown in FIGS. 22-24. The capacitance touch sensor is similar to the capacitance sensor described in connection with the illustrated embodiment of FIG. 15, but with one primary exception—though it should be understood that the capacitance sensor of FIG. 21 may be configured to include further exceptions according to one or more embodiments described herein.

In particular, the capacitance touch sensor of FIG. 21 includes a drive circuit and signal processing circuitry, both of which are similar to the drive circuit and the signal processing circuitry of FIG. 15. The capacitance touch sensor of FIG. 21 may also include a measurement circuit similar to the measurement circuit of FIG. 15, but including a transistor-based sensor electrode or a mutual inductance type sensor electrode substantially as set forth above in connection with FIG. 9. Although illustrated as including a transistor-based sensor electrode or a mutual inductance type sensor electrode, it should be understood that the present application is not so limited, and may include configurations having one type of sensor electrode. Other than the difference in sensor electrode type, the measurement circuit of FIG. 21 includes the same components as the measurement circuit of FIG. 15 described herein. The measurement circuit of FIG. 21 may be incorporated into one or more or all of the measurement stages described in connection with FIG. 19.

Figure 25:
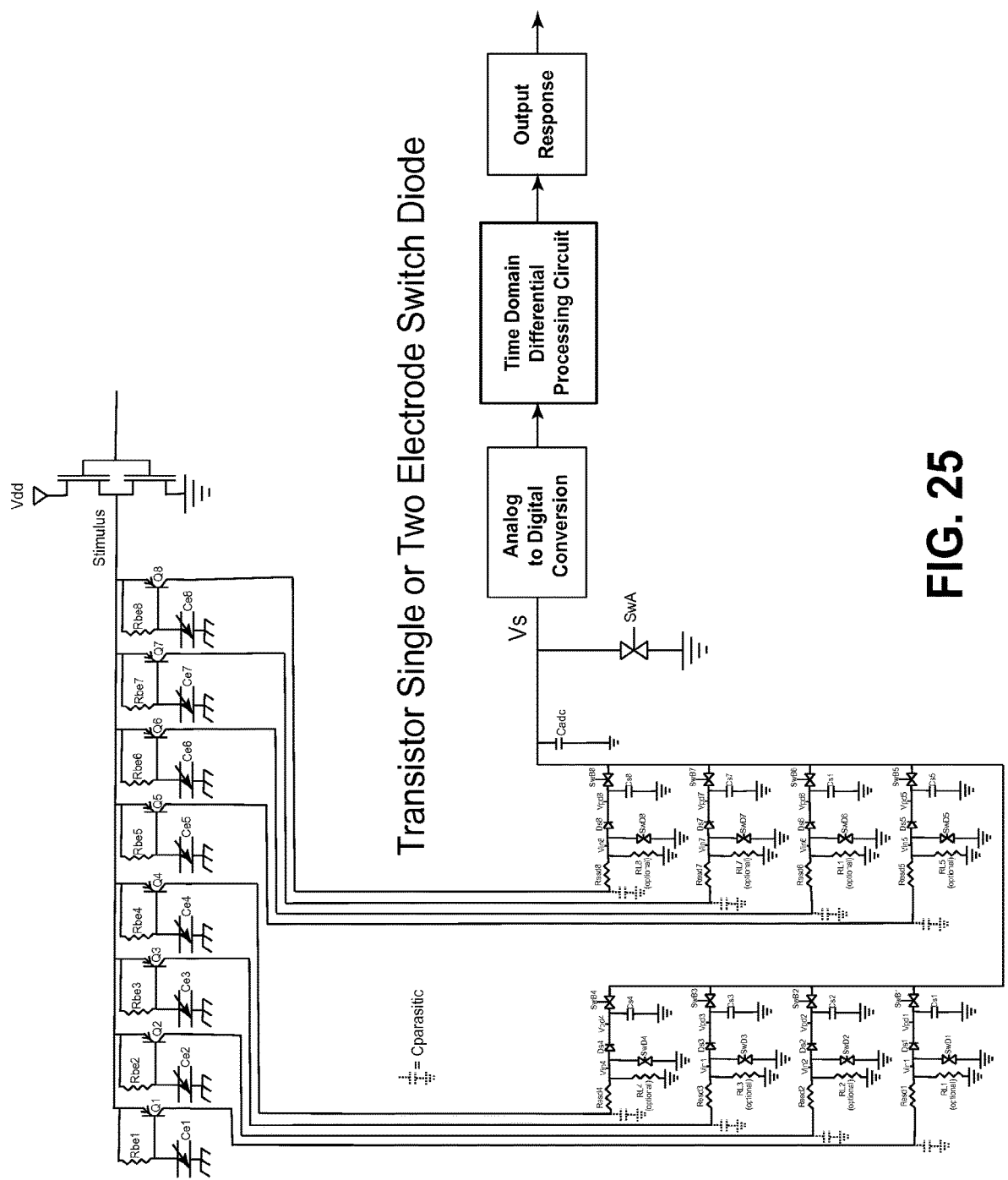
FIG. 25 is a circuit diagram of a capacitive touch sensor in accordance with an eighth embodiment.
Figure 26:
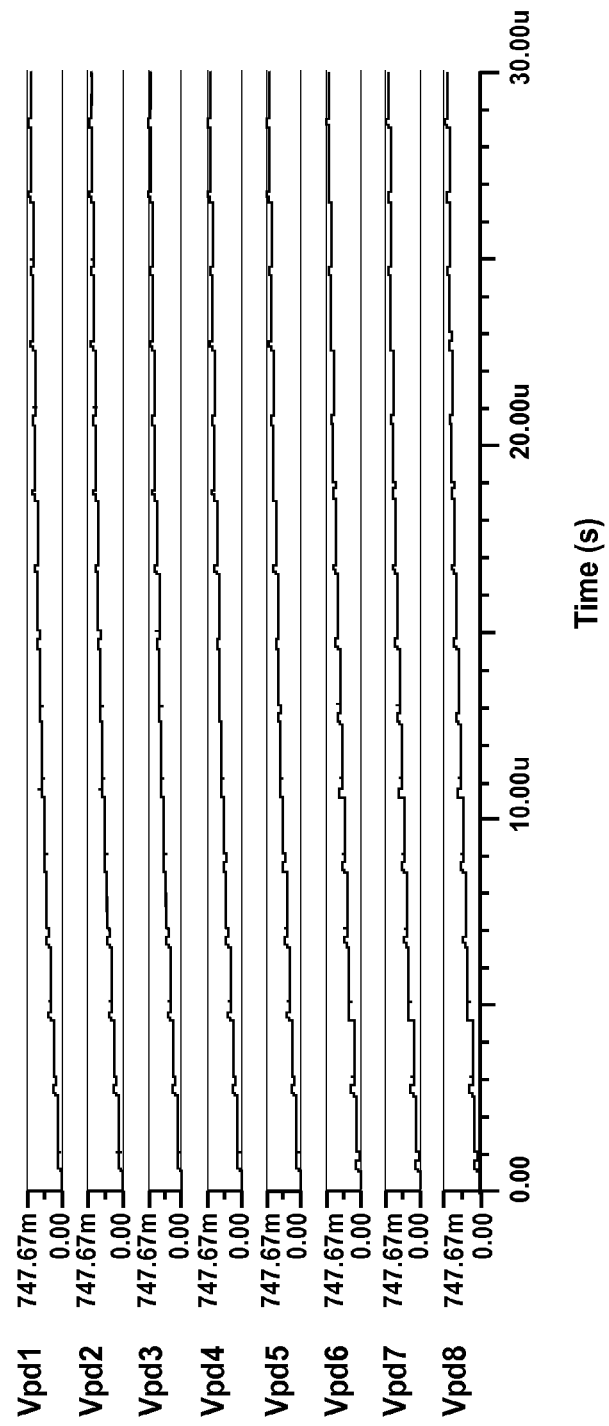
FIG. 26 is a timing diagram of the capacitive touch sensor of FIG. 25.

FIG. 25 illustrates an electrical schematic and block diagram of a capacitive touch sensor in accordance with an eighth embodiment. In the illustrated embodiment of FIG. 25, an electrical schematic and block diagram of a multi-electrode capacitance sensor or an array-type capacitance sensor is shown. A timing diagram associated with one or more operational states of the illustrated embodiment are shown in FIG. 26. The capacitive touch sensor is similar to the capacitive touch sensor of FIG. 21, but has been configured to sense multiple capacitive electrodes. In particular, the sensor of FIG. 25 includes measurement circuitry configured to assess multiple samples generated by drive circuitry, and to provide an output indicative of the multiple samples to signal processing circuitry. The measurement circuitry includes several measurement stages, each associated with a sensor electrode driven by the drive circuitry. The components incorporated into the capacitance sensor are nearly the same as the capacitance sensor, with the exception of including a transistor-based sensor electrode or a mutual inductance type sensor electrode configuration described in connection with the illustrated embodiment of FIG. 21.

Figure 27:
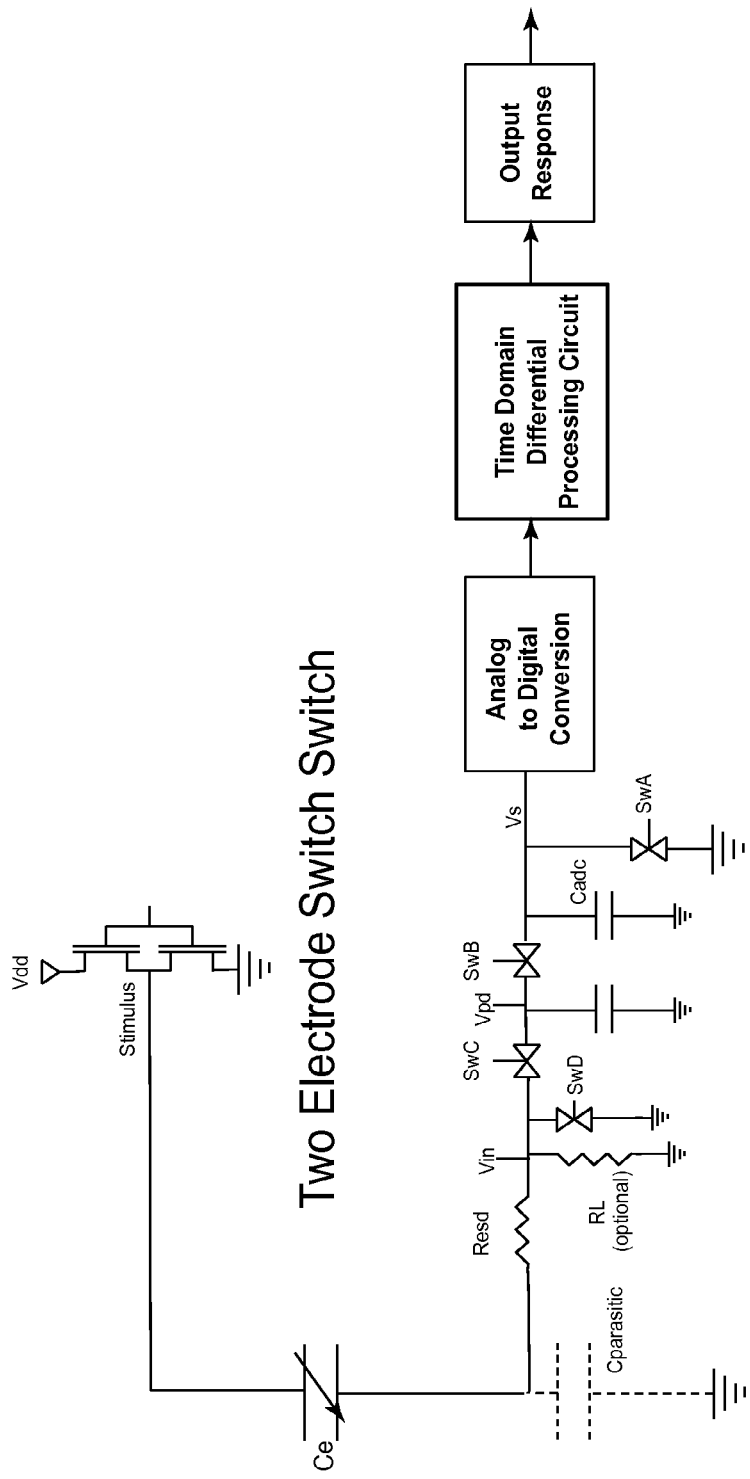
FIG. 27 is a circuit diagram of a capacitive touch sensor in accordance with a ninth embodiment.
Figure 28:
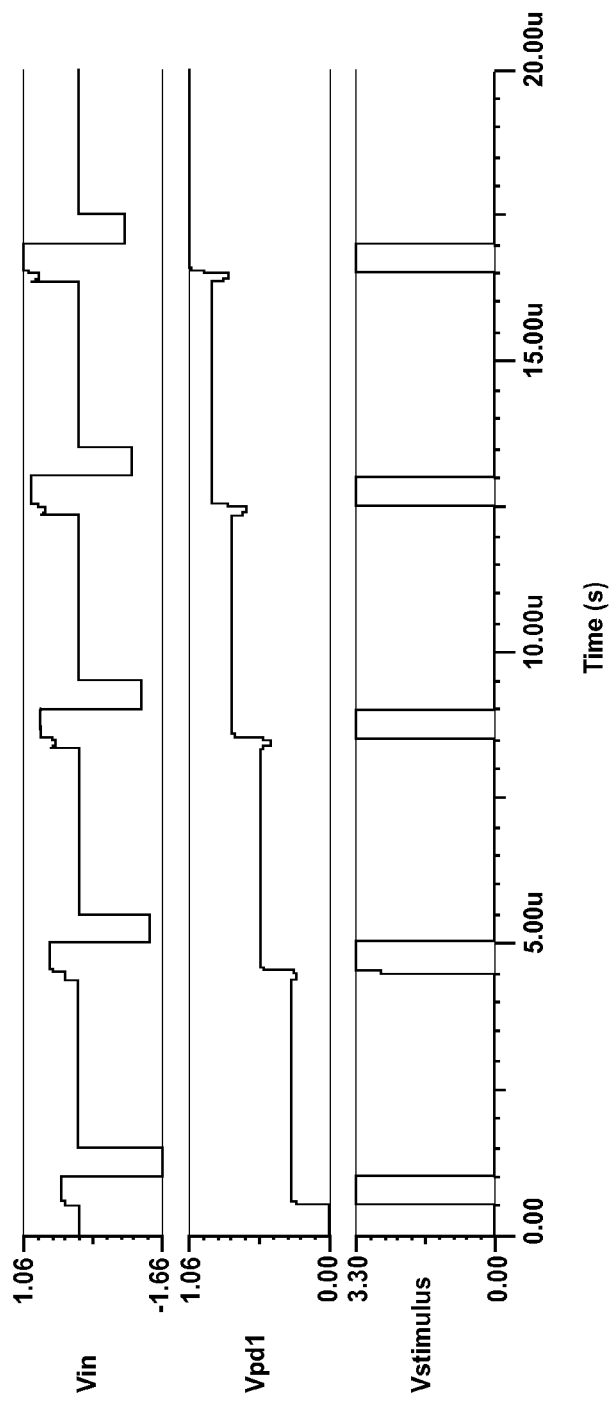
FIG. 28 is a first timing diagram of the capacitive touch sensor of FIG. 27.
Figure 29:
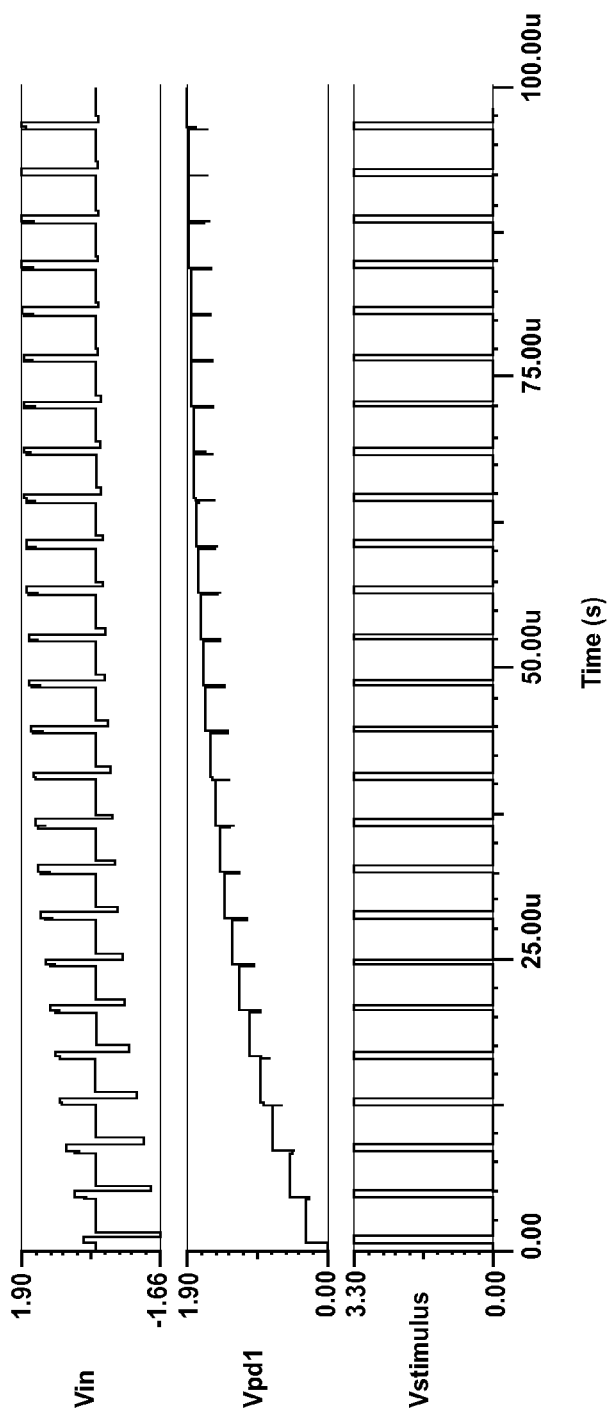
FIG. 29 is a second timing diagram of the capacitive touch sensor of FIG. 27.
Figure 30:
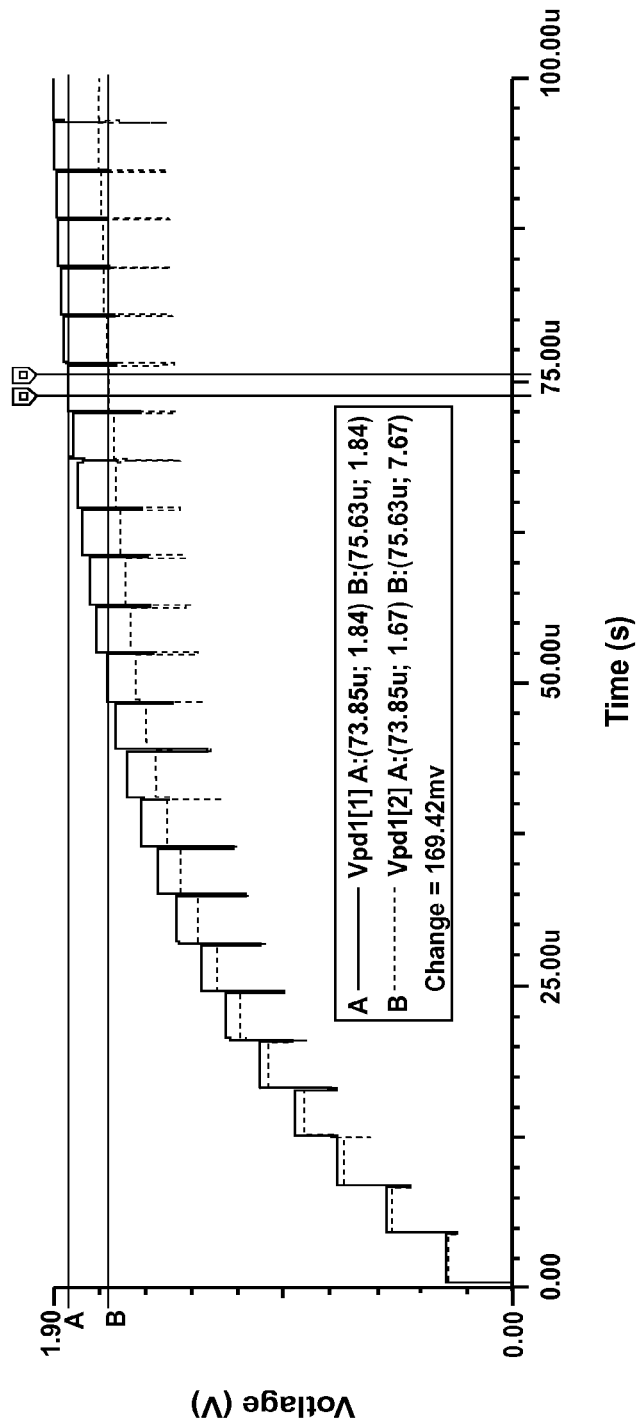
FIG. 30 is a third timing diagram of the capacitive touch sensor of FIG. 27.

FIG. 27 illustrates a circuit diagram of a capacitive touch sensor in accordance with a ninth embodiment. Timing diagrams associated with one or more operational states of the capacitive touch sensor of FIG. 27 are shown in FIGS. 28 through 30. The capacitive touch sensor of FIG. 27 is similar to the capacitive touch sensor of FIG. 15, except that the peak detector diode (Ds) is replaced with a peak detector switch (SwC). Unlike the peak detector diode (Ds), the peak detector switch (SwC) does not automatically turn on or off. That is, the peak detector diode (Ds) automatically transitions between conducting and non-conducting states in dependence on the voltage drop across the anode and cathode of the diode (Ds). The peak detector switch (SwC) enables control over whether voltage is applied to a peak detector capacitor (Ca) under circumstances different from that of the peak detector diode (Ds). For example, the peak detector switch (SwC) may be activated by the controller during times at which the peak detector diode (Ds) would be deactivated, and conversely, the peak detector switch (SwC) may be deactivated during times at which the peak detector diode (Ds) would be activated.

Figure 31:
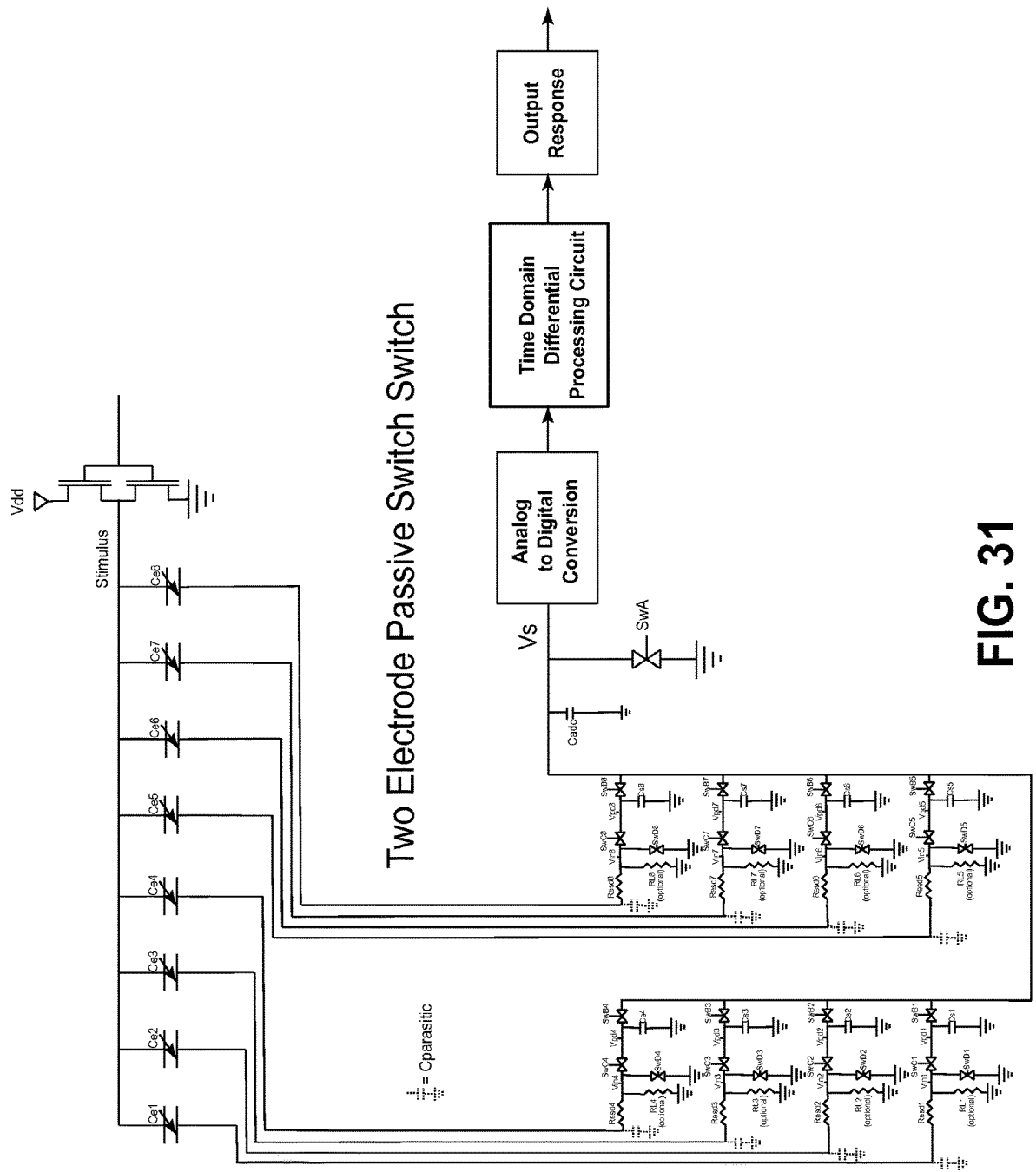
FIG. 31 is a circuit diagram of a capacitive touch sensor in accordance with a tenth embodiment.
Figure 32:
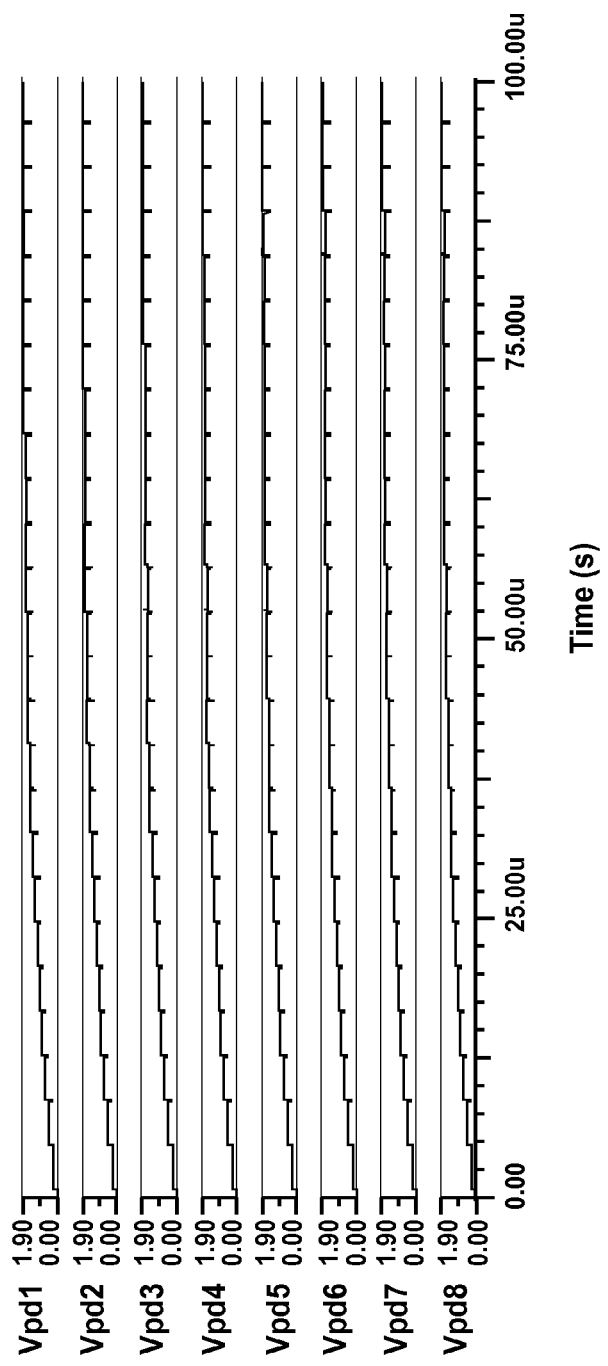
FIG. 32 is a timing diagram of the capacitive touch sensor of FIG. 31.

FIG. 31 illustrates a circuit diagram of a capacitive touch sensor in accordance with a tenth embodiment. FIG. 32 illustrates a timing diagram associated with one or more operational states of the capacitive touch sensor of FIG. 31. The capacitive touch sensor of FIG. 31 is similar to the capacitive touch sensor of FIG. 27, except that the capacitive touch sensor of FIG. 31 includes eight measurement stages corresponding to each of eight measurement electrodes (Ce1, Ce2 ... Ce8). Each measurement stage includes the components of the measurement circuit of FIG. 31 above, including eight peak detector switches (SwC1, SwC2 ... SwC8). As noted above, the measurement stage includes the portion of the measurement circuit that detects the peak self-capacitance or the peak mutual capacitance for a given electrode or electrode pair. In the embodiment illustrated in FIG. 31, there are eight measurement stages, each corresponding to one of the measurement capacitors (Ce1, Ce2 ... Ce8). Each measurement stage is coupled to the sample-and-hold capacitor (Cadc), which provides a DC output to the signal processing circuit as noted above.

Figure 33:
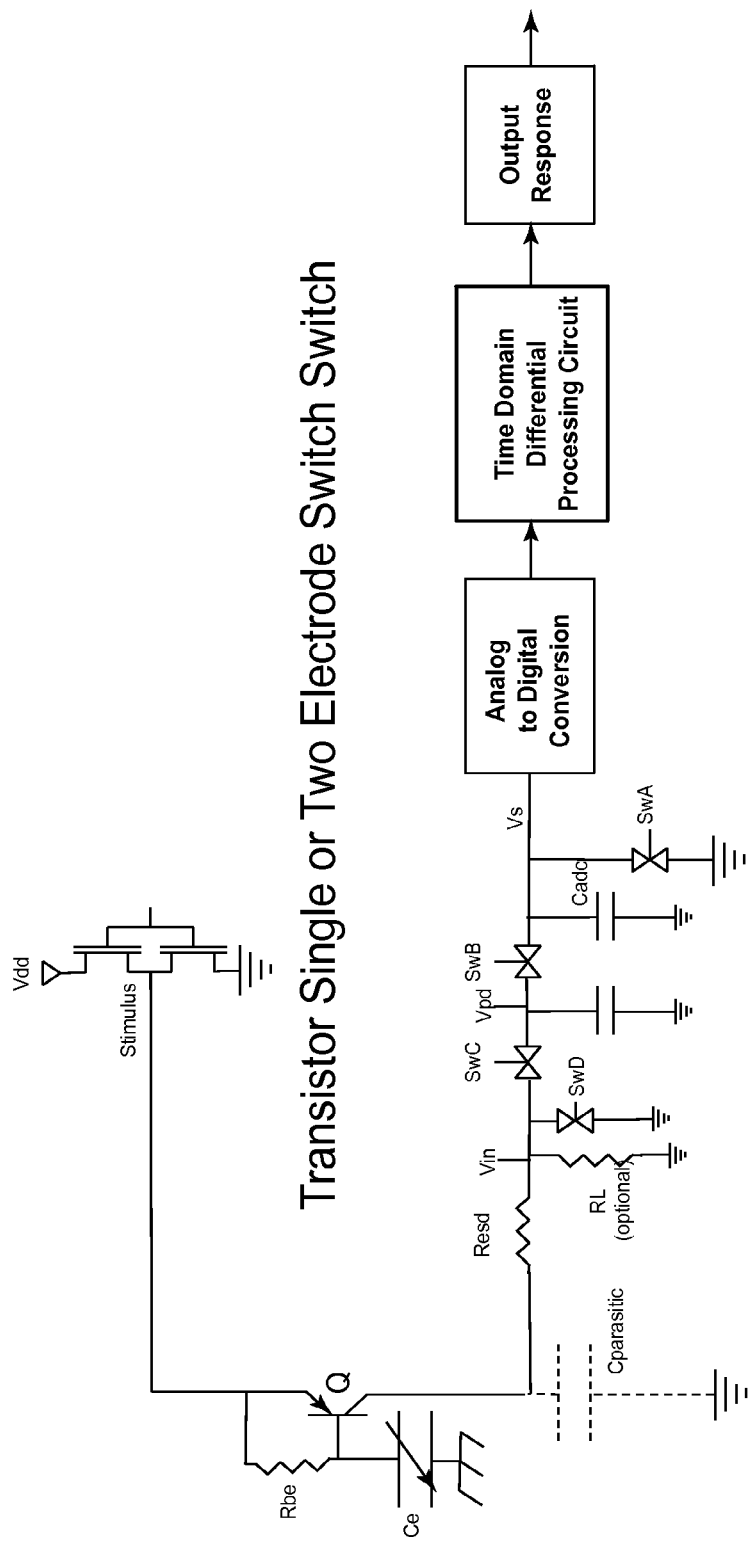
FIG. 33 is a circuit diagram of a capacitive touch sensor in accordance with an eleventh embodiment.
Figure 34:
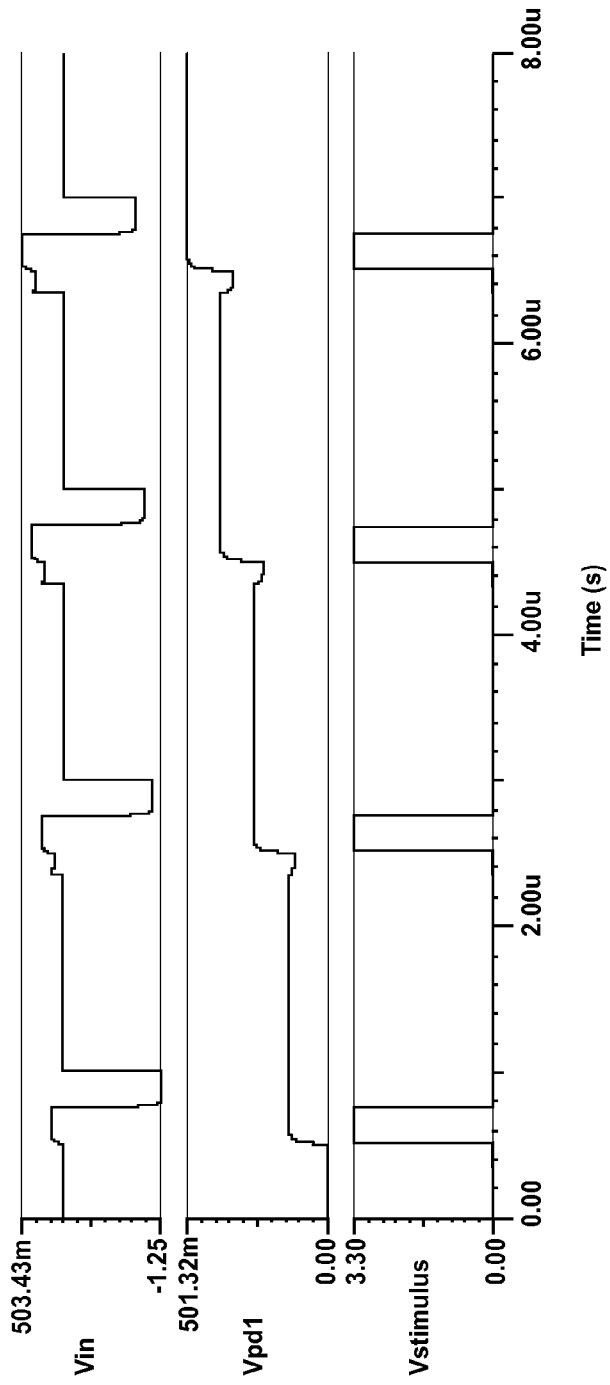
FIG. 34 is a first timing diagram of the capacitive touch sensor of FIG. 33.
Figure 35:
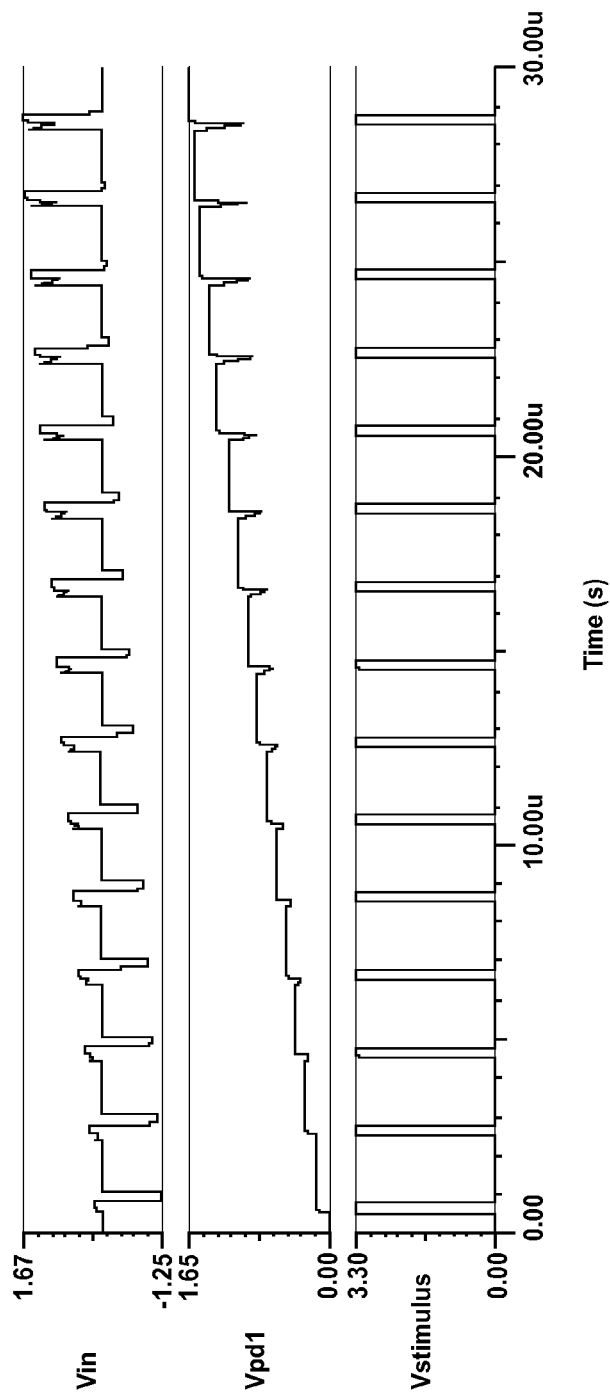
FIG. 35 is a second timing diagram of the capacitive touch sensor of FIG. 33.
Figure 36:
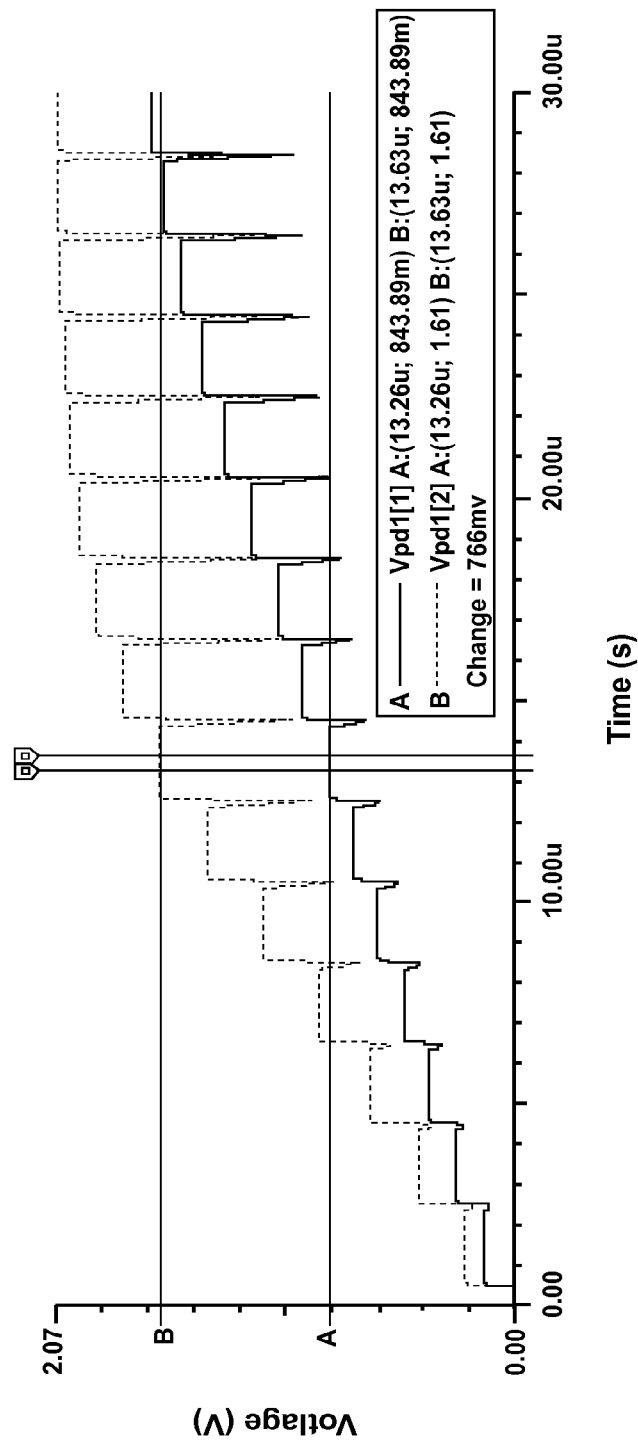
FIG. 36 is a third timing diagram of the capacitive touch sensor of FIG. 33.

FIG. 33 illustrates a circuit diagram of a capacitive touch sensor in accordance with an eleventh embodiment. Timing diagrams associated with one or more operational states of the capacitive touch sensor of FIG. 33 are shown in FIGS. 34 through 36. The capacitive touch sensor of FIG. 33 is similar in structure and function to the capacitive touch sensor of FIG. 27, except the dual-electrode measurement capacitor (Ce) for measurement mutual capacitance is replaced with a transistor-controlled electrode for measuring self-capacitance. In particular, a PNP transistor (Q) includes an emitter that is coupled to the voltage source (Vdd), a base coupled to a resistor (Rbe), and a collector coupled to the peak detector switch (SwC). In operation, the measurement electrode (Ce) and the resistor (Rbe) form a delay network. For example, the stimulus voltage causes a voltage to develop between the emitter and the base of the PNP transistor (Q), causing a base current to flow. This will in turn cause collector current to flow that is proportional to the gain of the transistor (Q). If the capacitance of the measurement capacitor (Ce) increases due to a stimuli, for example a touch input, the collector current will increase, which will charge the peak detector capacitor (Cs) for a give pulse of stimulus.

Figure 37:
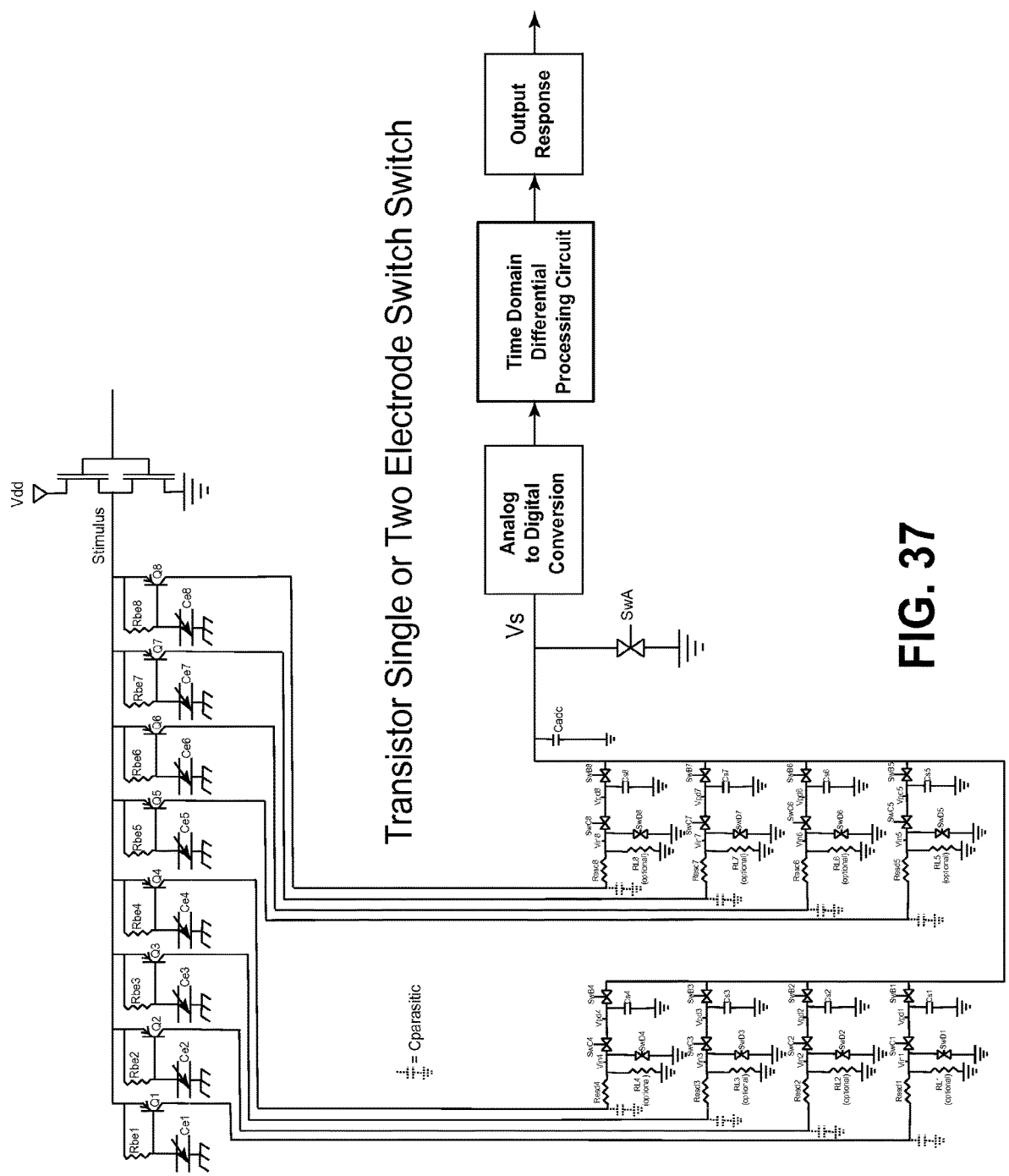
FIG. 37 is a circuit diagram of a capacitive touch sensor in accordance with a twelfth embodiment.
Figure 38:
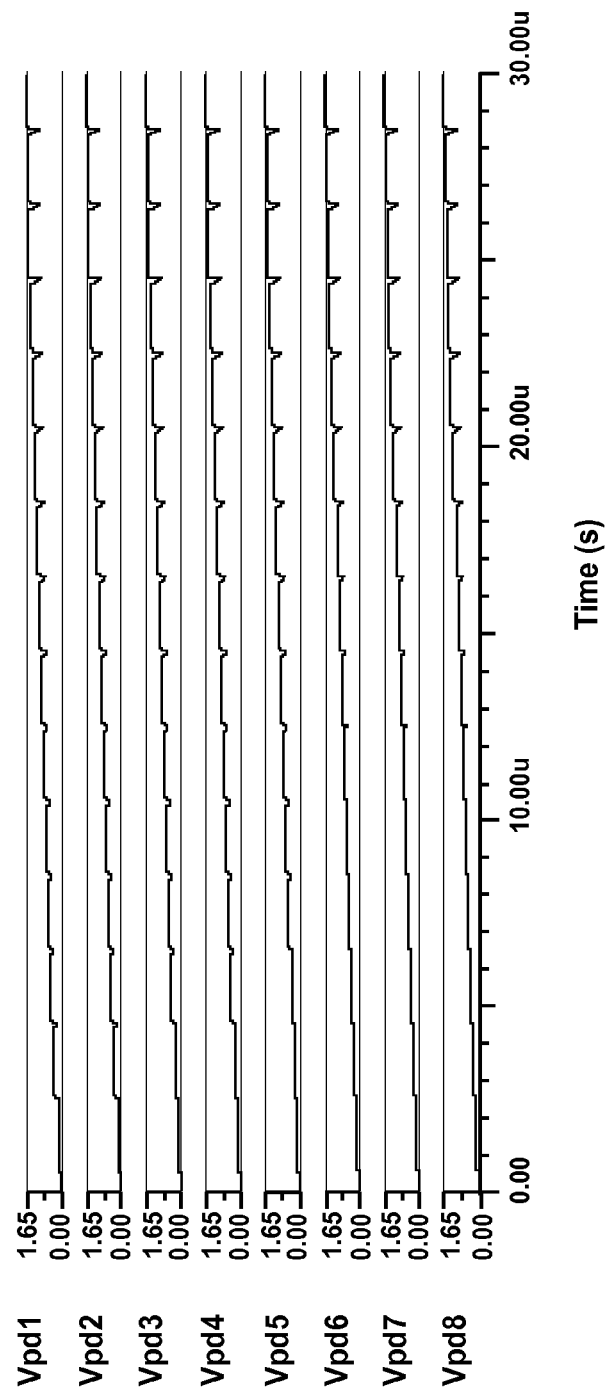
FIG. 38 is a timing diagram of the capacitive touch sensor of FIG. 37.

FIG. 37 illustrates a circuit diagram of a capacitive touch sensor in accordance with a twelfth embodiment. FIG. 38 illustrates a timing diagram associated with one or more operational states of the capacitive touch sensor of FIG. 37. The capacitive touch sensor of FIG. 37 is similar to the capacitive touch sensor of FIG. 33, except that the capacitive touch sensor of FIG. 37 includes eight transistor-controlled electrodes (Ce1, Ce2 . . . Ce8) and eight measurement stages. Each measurement stage includes the components of the measurement circuit of FIG. 33 above, including eight peak detector switches (SwC1, SwC2 . . . SwC8). Each measurement stage detects the peak self-capacitance for a corresponding transistor-controlled electrode (Ce1, Ce2 . . . Ce8). Each measurement stage is coupled to the sample-and-hold capacitor (Cadc), which provides a DC output to the signal processing circuit as noted above.

Figure 39:
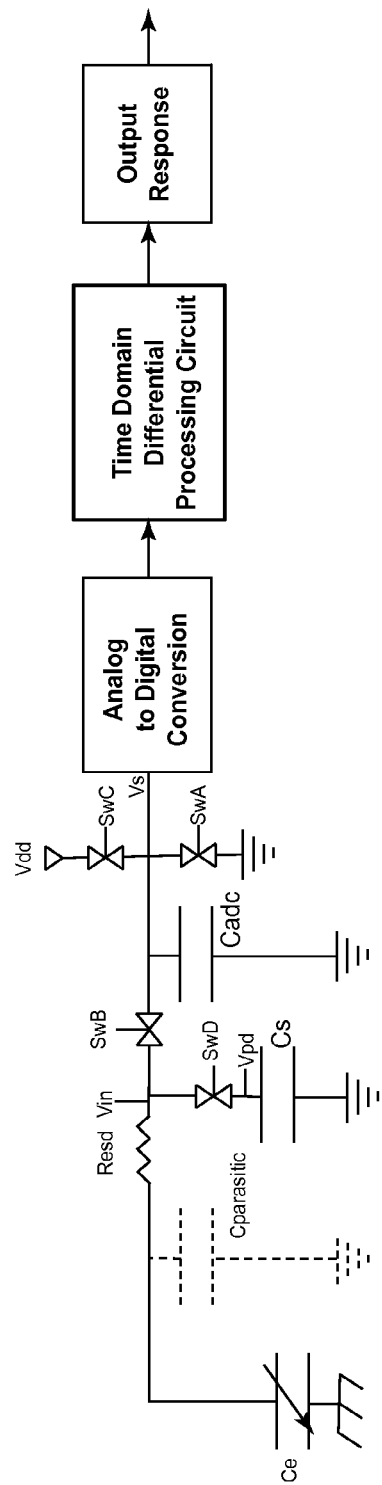
FIG. 39 is a circuit diagram of a capacitive touch sensor in accordance with a thirteenth embodiment.
Figure 40:
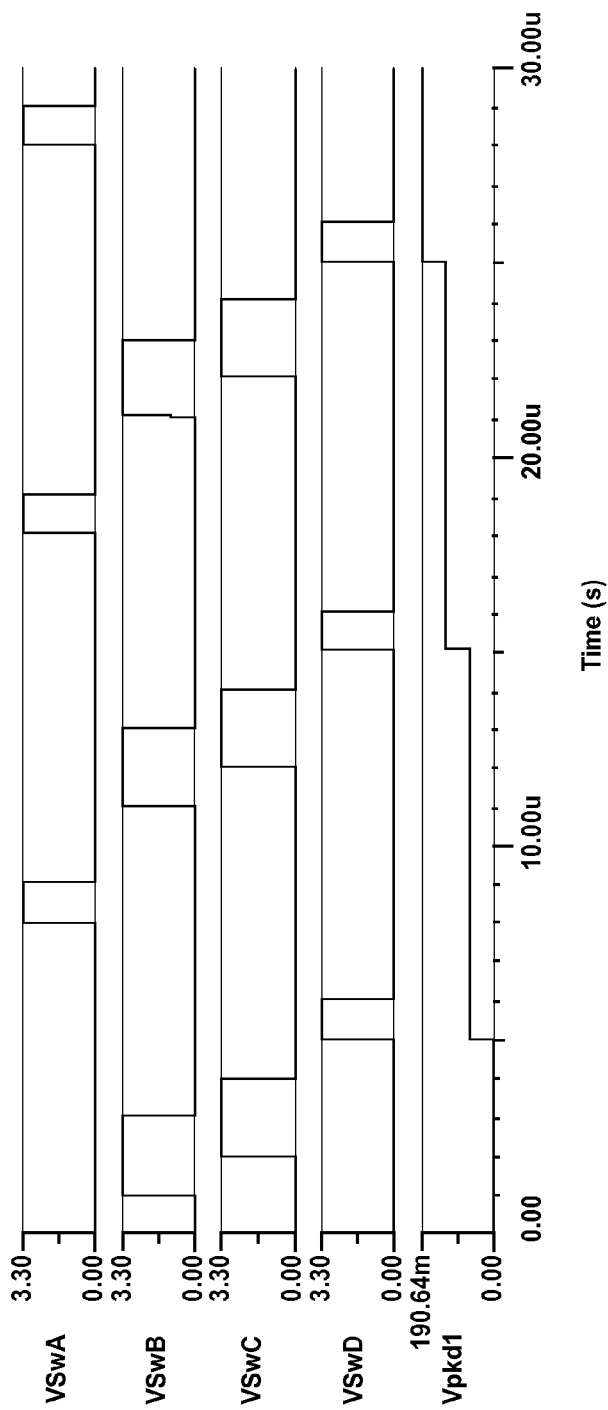
FIG. 40 is a first timing diagram of the capacitive touch sensor of FIG. 39.
Figure 41:
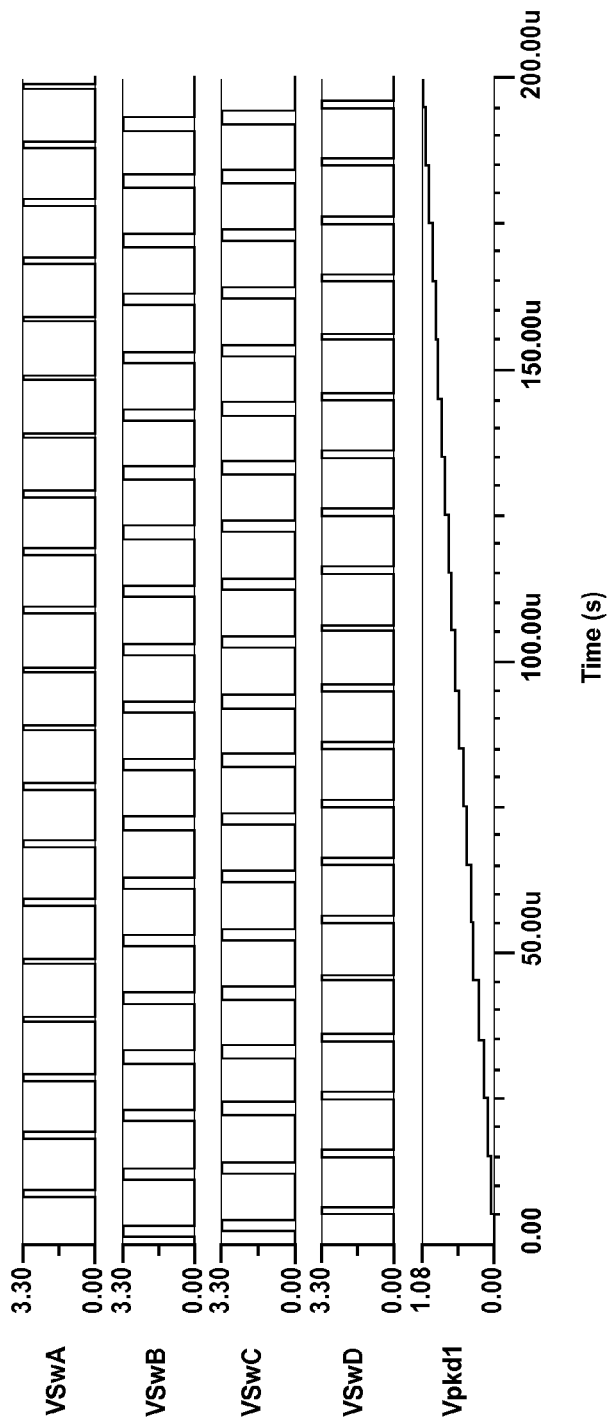
FIG. 41 is a second timing diagram of the capacitive touch sensor of FIG. 40.
Figure 42:
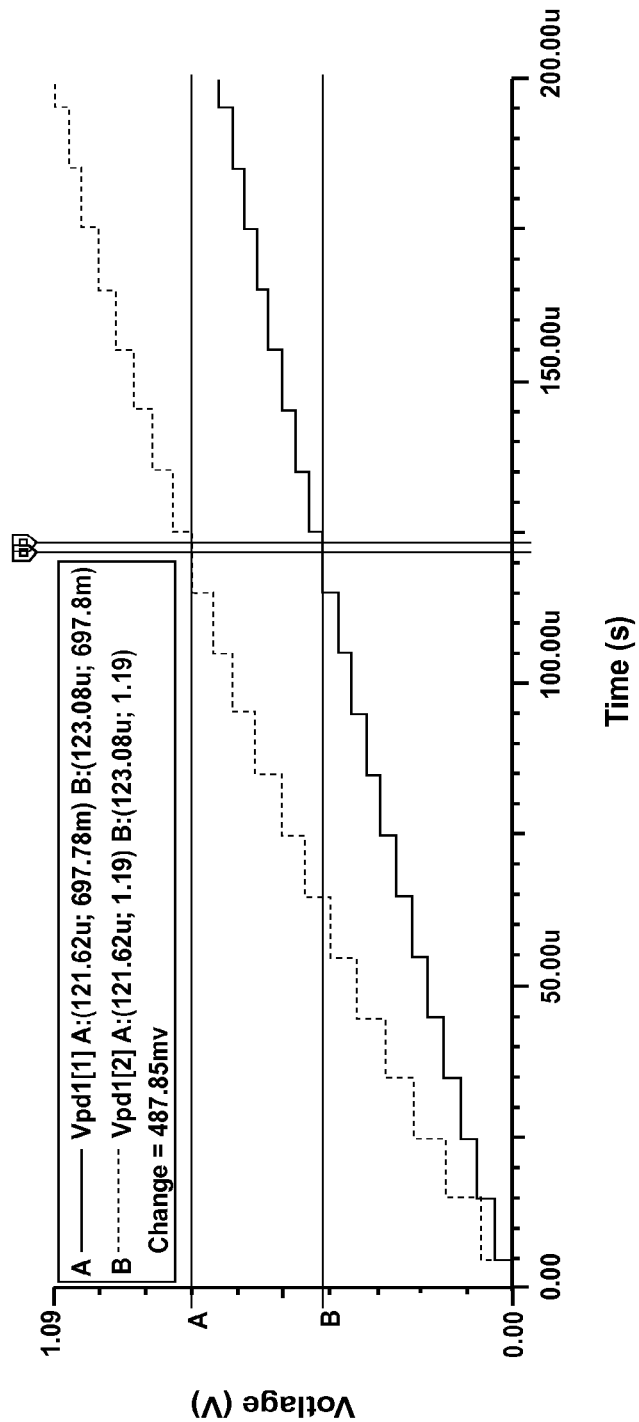
FIG. 42 is a third timing diagram of the capacitive touch sensor of FIG. 41.
Figure 43:
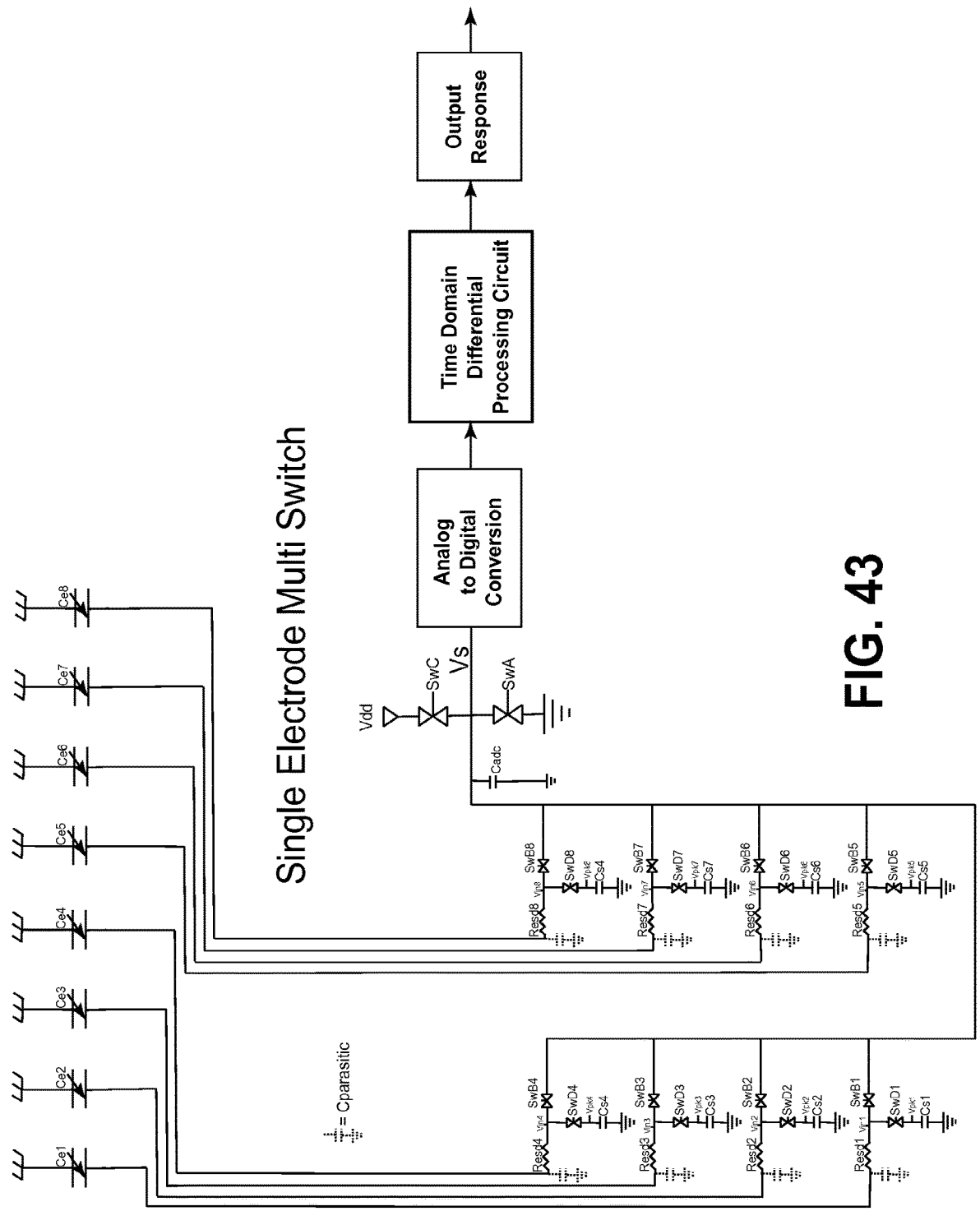
FIG. 43 is a circuit diagram of a capacitive touch sensor in accordance with a fourteenth embodiment.
Figure 44:
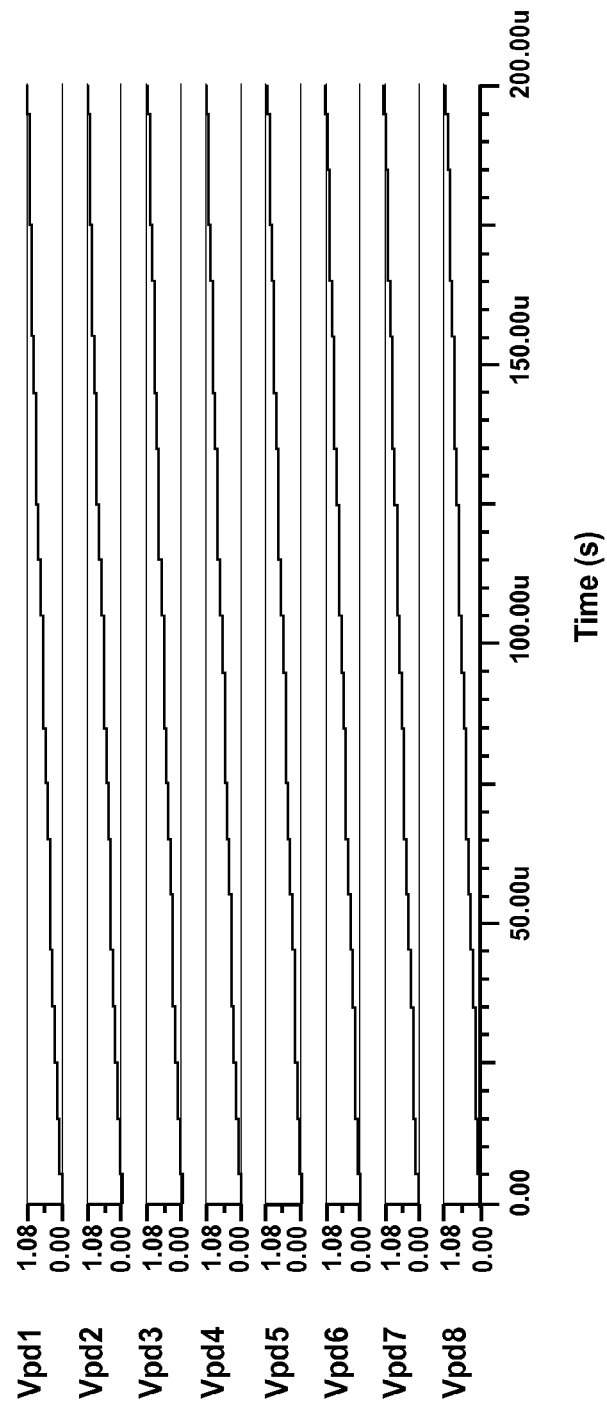
FIG. 44 is a timing diagram of the capacitive touch sensor of FIG. 43.
Figure 45:
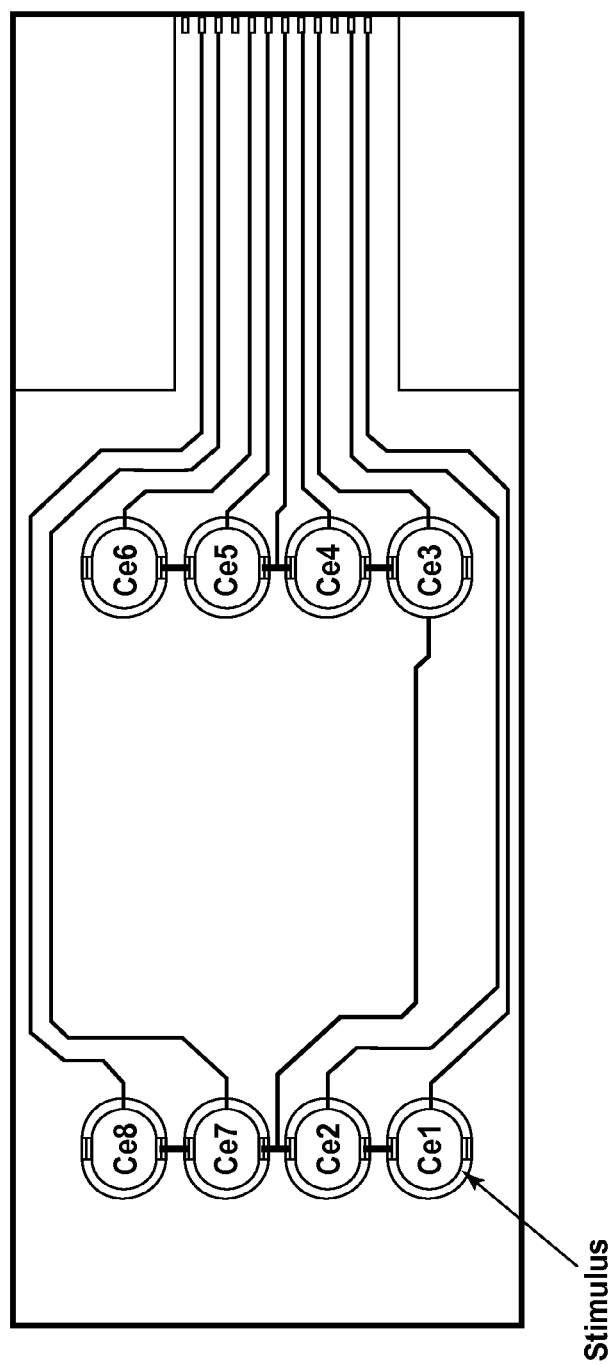
FIG. 45 is a depiction of eight single-electrodes for use with the foregoing embodiments using self-capacitance.

FIG. 39 illustrates a circuit diagram of a capacitive touch sensor in accordance with a thirteenth embodiment. Timing diagrams associated with one or more operational states of the capacitive touch sensor of FIG. 39 are shown in FIGS. 40 through 42. The capacitive touch sensor of FIG. 39 is similar in structure and function to the capacitive touch sensor of FIG. 33, except the voltage source (Vdd) is coupled to the peak detector capacitor (Cs), which is connected in parallel to the measurement capacitor (Ce). The voltage at the sample-and-hold capacitor (Cadc) is proportional to the capacitance at the measurement capacitor (Ce), which is then output to the signal processing circuit for digital signal processing. FIG. 43 illustrates a circuit diagram of a capacitive touch sensor in accordance with a fourteenth embodiment. FIG. 44 illustrates a timing diagram associated with one or more operational states of the capacitive touch sensor of FIG. 43. The capacitive touch sensor of FIG. 43 is similar to the capacitive touch sensor of FIG. 39, except that the capacitive touch sensor of FIG. 43 includes eight electrodes (Ce1, Ce2 . . . Ce8) and eight measurement stages. Each measurement stage includes the components of the measurement circuit of FIG. 39 above, including eight peak detector switches, and each measurement stage detects the peak self-capacitance for a corresponding measurement electrode (Ce1, Ce2 . . . Ce8). Each measurement stage is coupled to the sample-and-hold capacitor (Cadc), which provides a DC output to the signal processing circuit as noted above.

Figure 47:
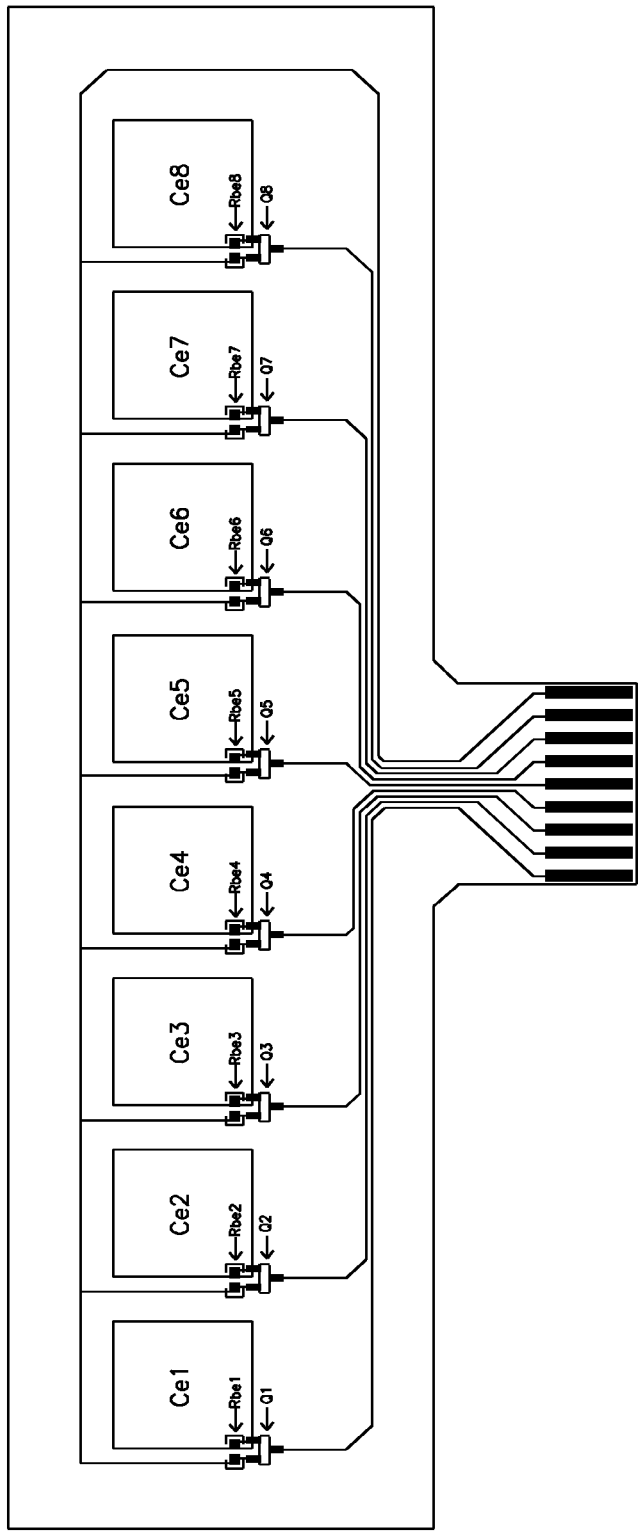
FIG. 47 is a depiction of eight dual-electrodes for use with the foregoing embodiments using self-capacitance with a transistor-electrode-pair.
Figure 48:
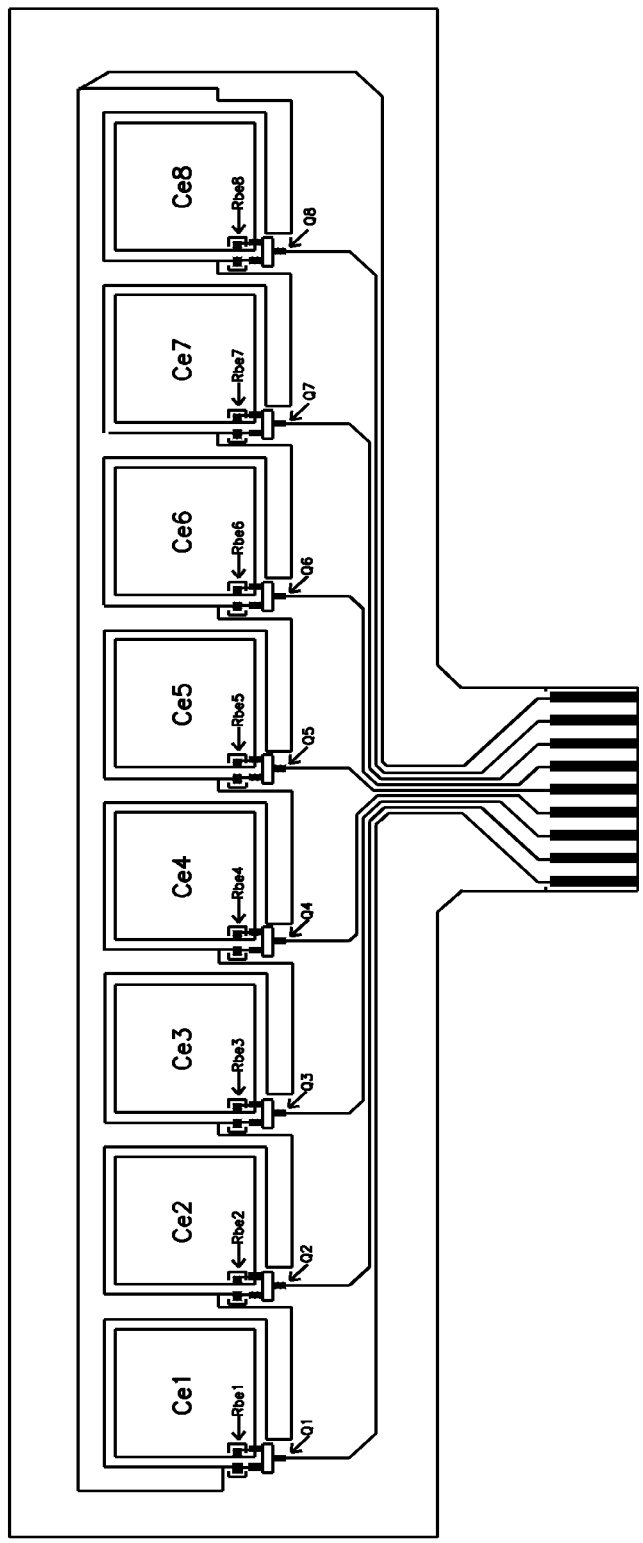
FIG. 48 is a depiction of eight dual-electrodes for use with the foregoing embodiments using mutual-capacitance with a transistor-electrode-pair.

FIGS. 45-48 include physical constructions for electrode structures for a capacitive touch sensor. In particular, the electrode structure of FIGS. 45 and 46 can be used in connection with the capacitive touch sensors of any of FIGS. 3-8, 21-26, and 33-38. The stimulus signal surrounds each of the electrodes (Ce1, Ce2 . . . Ce8) with traces that lead back to the edge of a sensor board, where the signals would be processed as described above. The electrode structure of FIG. 47 can be used in connection with the capacitive touch sensors of any of FIGS. 9-14, 21-26, and 33-38. The transistors may be located on the tail of the circuit or off the sensor board as shown in FIG. 47. The closer to the electrode that the transistors are located the better the isolation from parasitic capacitance, while also preventing cross coupling. The electrode structure of FIG. 48 can be used in connection with the capacitive touch sensors of any of FIGS. 9-14, 21-26 and 33-38. The stimulus is connected to an outer electrode that substantially surrounds the measurement electrodes (Ce1, Ce2 . . . Ce8). This configuration can provided better isolation between the measurement electrodes (Ce1, Ce2 . . . Ce8), thereby increasing water immunity. The transistors may also be located on the tail of the circuit or off the sensor board as shown in FIG. 47. The closer to the electrode that the transistors are located the better the isolation from parasitic capacitance, while also preventing cross coupling.

Figure 49:
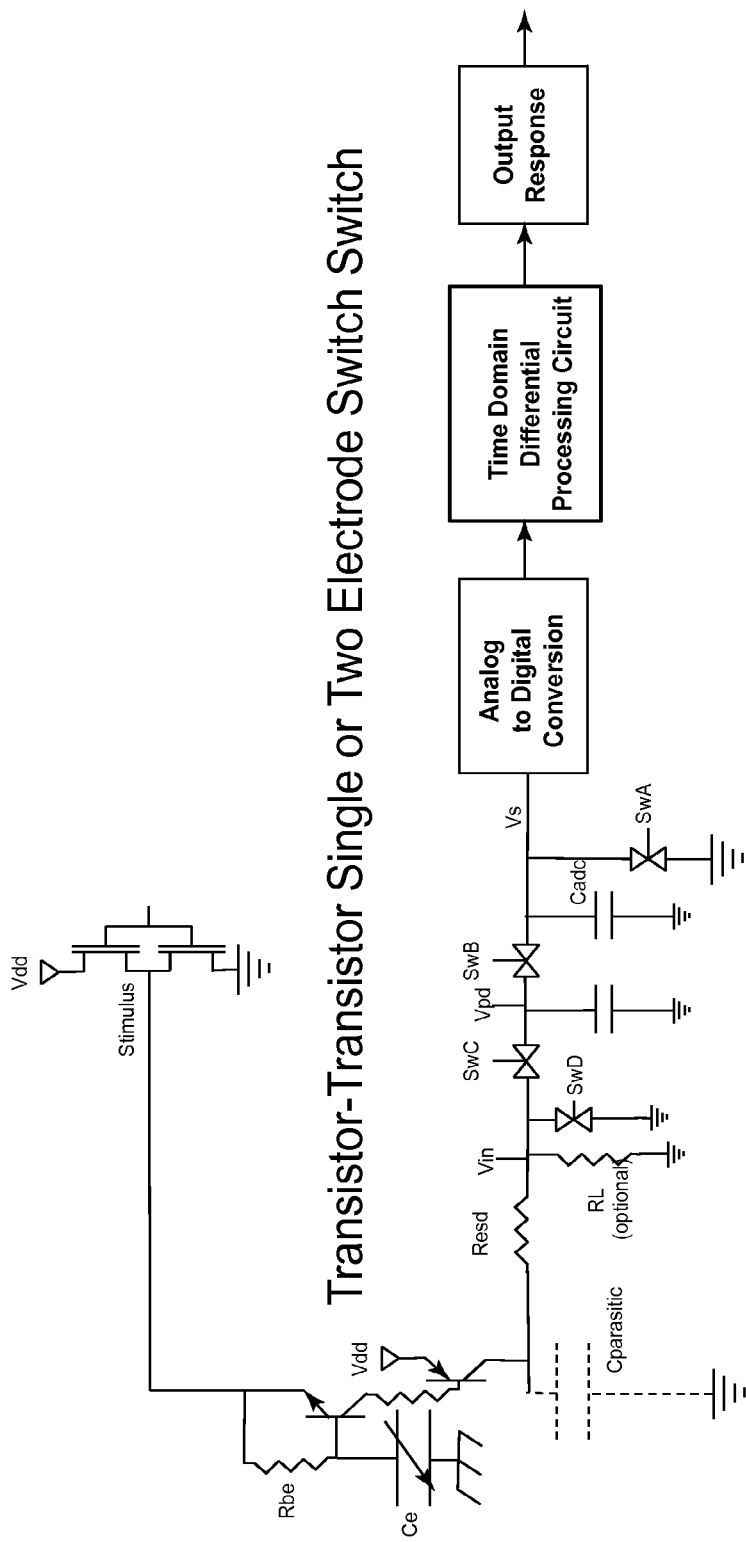
FIG. 49 is a circuit diagram of a capacitive touch sensor in accordance with a fifteenth embodiment.

FIG. 49 illustrates a circuit diagram of a capacitive touch sensor in accordance with a fifteenth embodiment. In the illustrated embodiment of FIG. 49, the transistor-based sensor electrode is a transistor-transistor type sensor. The transistor-transistor type sensor includes an NPN transistor that may aid in providing water immunity and isolation. In this configuration, if the signal output from the transistor-transistor type sensor is insufficient to obtain a satisfactory signal, an amplification stage may be included to increase the gain on the output signal. The amplification stage may be one of several different amplification topologies. In the illustrated embodiment, a PNP transistor is used as part of an amplification stage. The collector current of the NPN transistor may provide base current for the PNP transistor, which in turn amplifies and increases the space current by the gain of the PNP transistor at the collector of the PNP transistor. The signal output at the collector of the PNP transistor may be assessed using any of the configurations or embodiments described herein. In the illustrated embodiment, the measurement circuit of FIG. 49 is configured similar to the measurement circuit of FIG. 27, but it should be understood that the measurement circuit of FIG. 49 may be configured differently.

The capacitive touch sensors shown above are described in connection with a Time Domain Differential Processing Circuit, while measuring multiple electrodes simultaneously. The capacitive touch sensors described above can be used with other capacitive measuring techniques, including those that rely on a comparison against a predetermined threshold. Even though not shown in all of the Figures, any of the inputs to the analog-to-digital converters can be preceded by an amplifying stage to increase the gain and thereby reduce the processing requirements of the signal processing circuit. While the Figures illustrate one stimulus line driving eight sensing return lines, the Figures do not limit the present invention to these configurations. For example, there can be multiple stimulus lines forming several drive rows with additional electrodes, with the electrodes forming a column and row matrix. For example, each additional drive line may be turned on and off periodically to allow the sensing columns to simultaneously process each drive row, sampling each row, and simultaneously sensing the outputs from each row's electrodes.

The above description is that of current embodiments. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A method comprising:
strobing a first electrode having a capacitance with respect to a second electrode with a time-varying waveform over a first measurement period;
strobing the first electrode with a time-varying waveform over a second measurement period;
electrically coupling a processing unit to the first and second electrodes;
registering a first touch signature in response to an object approaching one of the first or second electrode, the first touch signature occurring over a total time domain (T) between a first time and a second time, between a first capacitance and a second capacitance, wherein the first touch signature includes a rate of change (ds/dt) of the between the first and second capacitance in combination with at least one parameter of the first touch signature selected from the group consisting essentially, of an interval change in capacitance (ds) during the total time domain (T) where the interval change in capacitance (ds) is less than a total change in capacitance(S) for the first touch signature, an interval time domain (dt) corresponding to the interval change in capacitance (ds), wherein the interval time domain (dt) is less than the total time domain (T) for the first touch signature, and combinations thereof.

2. The method according to claim 1 wherein calculating differential measurement of one of ds, dt, ds/dt, S, T, and combinations thereof is done simultaneously.

3. The method according to claim 1 further comprising disposing the first and second of electrodes in multiple planes above a substrate.

4. The method claim 1, further comprising operatively coupling an A/D converter to the first electrode, the A/D converter being configured to read a signal from the first electrode.

5. The method claim 1, further comprising operatively coupling a capacitor to the first electrode, the capacitor being configured to read a signal from the first electrode.

6. The method according to claim 1 further comprising calculating one of ds, dt, ds/dt, S, T, and combinations thereof.

7. The method according to claim 1 further comprising disposing a substrate in proximity to the first and second electrodes, and calculating a substrate relative movement.

8. The method according to claim 1 further comprising conducting a first signature profile decision based on if ds is less than a first value for a given dt, too determined to be a touch event did not occur.

9. The method according to claim 1 further comprising providing one of a hardware filter and a software filter.

10. The method according to claim 1 further comprising calculating measurement of one of ds, dt, ds/dt, S, T, and combinations thereof at one of the first and second electrodes.

11. The method according to claim 1 further comprising providing a third electrode configured to provide stimulus to the first and second electrodes.

12. The method according to claim 11 wherein the third electrode provides stimulus to one of the first and second electrodes selected from the group consisting of ground, v−, v+, a periodic signal and combinations thereof.

13. The method according to claim 1, wherein the second electrode is one of a plurality of second electrodes.

14. The method according to claim 12, wherein the first electrode is common to the plurality of second electrodes.

15. The method according to claim 12, wherein the plurality of second electrodes are arranged in an array.

16. The method according to claim 12 further comprising filtering the signal prior to calculating measurement of one of ds, dt, ds/dt, S, T, and combinations thereof from the first electrode.

17. The method according to claim 12 further comprising filtering the signal prior to calculating measurement of one of ds, dt, ds/dt, S, T, and combinations thereof from the first and second electrodes.

18. The method according to claim 16 further comprising conducting a second signature profile decision based on if ds is greater than a second value for a given dt, too determined to be a touch event did not occur.

* * * * *